(12) United States Patent
Ueno et al.

(10) Patent No.: US 9,867,917 B2
(45) Date of Patent: Jan. 16, 2018

(54) MEDICAL MATERIAL AND HOLLOW FIBER MEMBRANE MODULE

(75) Inventors: Yoshiyuki Ueno, Otsu (JP); Masaki Fujita, Otsu (JP); Hiroyuki Sugaya, Otsu (JP); Kazuyuki Hashimoto, Otsu (JP); Hiroyuki Terasaka, Otsu (JP); Ryo Koganemaru, Otsu (JP)

(73) Assignee: Toray Industries, Inc., Tokyo (JP)

( * ) Notice: Subject to any disclaimer, the term of this patent is extended or adjusted under 35 U.S.C. 154(b) by 664 days.

(21) Appl. No.: 13/997,459

(22) PCT Filed: Dec. 27, 2011

(86) PCT No.: PCT/JP2011/080246
§ 371 (c)(1),
(2), (4) Date: Aug. 1, 2013

(87) PCT Pub. No.: WO2012/091028
PCT Pub. Date: Jul. 5, 2012

(65) Prior Publication Data
US 2013/0306544 A1    Nov. 21, 2013

(30) Foreign Application Priority Data

Dec. 28, 2010  (JP) ................................. 2010-292170
Apr. 11, 2011  (JP) ................................. 2011-087126

(51) Int. Cl.
  *A61M 1/16*  (2006.01)
  *A61M 1/36*  (2006.01)
  (Continued)

(52) U.S. Cl.
  CPC ............. *A61M 1/16* (2013.01); *A61L 33/062* (2013.01); *A61M 1/3673* (2014.02);
  (Continued)

(58) Field of Classification Search
  CPC ....... A61L 33/062; B01D 61/28; B01D 63/24; B01D 63/243; B01D 63/246; B01D 69/02;
  (Continued)

(56) References Cited

U.S. PATENT DOCUMENTS 3,339,341 A  *  9/1967  Maxwell ................ B01D 63/02
                                                95/53
4,376,095 A  *  3/1983  Hasegawa ........... A61M 1/1698
                                                128/DIG. 3
(Continued)

FOREIGN PATENT DOCUMENTS

JP     04-300636     10/1992
JP     06-165926      6/1994
(Continued)

OTHER PUBLICATIONS

International Search Report dated Feb. 21, 2012, application No. PCT/JP2011/080246.

(Continued)

*Primary Examiner* — Lucas Stelling
*Assistant Examiner* — Angel Olivera
(74) *Attorney, Agent, or Firm* — RatnerPrestia

(57) ABSTRACT

The present invention provides a medical material and a blood purification apparatus each having high anti-thrombotic properties and high safety. The apparatus is produced by incorporating therein a medical material which has a hydrophilic copolymerization polymer present on a surface thereof which is to be in contact with blood, wherein particulate protuberances each having a particle diameter of 50 nm or more are present on the surface which is to be in contact with blood at a density of 3 particles/μm$^2$ or less and the relaxation time of adsorbed water in the hydrophilic (Continued)

copolymerization polymer is $2.5 \times 10^{-8}$ seconds or shorter and $5.0 \times 10^{-10}$ seconds or longer at $-40°$ C.

4 Claims, 6 Drawing Sheets

(51) Int. Cl.

| | |
|---|---|
| *A61L 33/06* | (2006.01) |
| *B01D 63/02* | (2006.01) |
| *B01D 67/00* | (2006.01) |
| *B01D 69/02* | (2006.01) |
| *B01D 69/08* | (2006.01) |
| *B01D 71/76* | (2006.01) |
| *B01D 71/68* | (2006.01) |

(52) U.S. Cl.
CPC ......... *B01D 63/02* (2013.01); *B01D 67/0088* (2013.01); *B01D 69/02* (2013.01); *B01D 69/084* (2013.01); *B01D 71/76* (2013.01); *A61M 1/1623* (2014.02); *A61M 1/1625* (2014.02); *A61M 1/1627* (2014.02); *A61M 1/3672* (2013.01); *B01D 71/68* (2013.01); *B01D 2323/02* (2013.01)

(58) Field of Classification Search
CPC .... B01D 69/08; B01D 69/081; B01D 69/082; B01D 69/084; B01D 69/085; B01D 69/087; B01D 69/088; B01D 63/02; B01D 63/021; B01D 63/022; B01D 63/023; A61M 1/16; A61M 1/18
See application file for complete search history.

(56) References Cited

U.S. PATENT DOCUMENTS

| | | | |
|---|---|---|---|
| 4,720,343 A | 1/1988 | Walch et al. | |
| 6,409,024 B1* | 6/2002 | Nakashima | A61M 1/16 210/321.79 |
| 2011/0017654 A1* | 1/2011 | Ueno | B01D 63/02 210/321.6 |

FOREIGN PATENT DOCUMENTS

| | | |
|---|---|---|
| JP | 10-165777 | 6/1998 |
| JP | 2-18695 B2 | 12/1998 |
| JP | 2009-262147 A | 11/2009 |
| JP | 2010-36127 A | 2/2010 |
| JP | 2010-104984 A | 5/2010 |
| WO | WO2008/093654 A1 | 8/2008 |
| WO | WO2009/123088 A1 | 10/2009 |

OTHER PUBLICATIONS

Chiaki Yoshikawa et al., Protein Repellency of Well-Defined, Concentrated Poly(2-hydroxyethyl methacrylate) Brushes by the Size-Exclusion Effect Macromolecules 2006, 39, 2284-2290, vol. 39, No. 6, 2006.

* cited by examiner

MEDICAL MATERIAL AND HOLLOW FIBER MEMBRANE MODULE

CROSS REFERENCE TO RELATED APPLICATIONS

This application is the U.S. National Phase application of PCT/JP2011/080246, filed Dec. 27, 2011, and claims priority to Japanese Patent Application No. 2010-292170, filed Dec. 28, 2010, and Japanese Patent Application No. 2011-087126, filed Apr. 11, 2011, the disclosures of each being incorporated herein by reference in their entireties for all purposes.

FIELD OF THE INVENTION

The present invention relates to a medical material having anti-thrombotic properties which can be used suitable in use applications for which it is required to treat blood or a blood component, particularly in blood purification apparatus such as an artificial kidney and other use applications for which high levels of membrane performance, blood compatibility and safety are required.

BACKGROUND OF THE INVENTION

A medical material to be contacted with a body fluid, such as an artificial blood vessel, a catheter, a blood bag and a blood treatment apparatus, has been required to have high anti-thrombotic properties. Examples of the blood treatment apparatus include an artificial kidney, an artificial liver, an artificial lung, a blood component adsorbent device and a plasma separator. In the present invention, a blood treatment apparatus is synonymous with a blood purification apparatus, and a hollow fiber membrane module refers to a hollow fiber membrane-type blood treatment apparatus.

For example, in a hollow fiber membrane for use in an artificial kidney (of which the schematic cross sectional views are shown in FIGS. 1 and 2), the deposition of a protein or the deposition/activation of platelets can cause the coagulation of blood. When a protein or the like is deposited onto a membrane, even if led to the coagulation of blood, pores in the membrane are blocked out and become small, resulted in the deterioration in the performance. When the performance of the membrane is altered rapidly within a short time, there is a concern about the increase in burden on a living body.

For the purpose of solving these problems, it has been attempted to hydrophylize a hollow fiber membrane and various studies have been made for this purpose. For example, a method is disclosed, in which polyvinylpyrrolidone, which is a hydrophilic polymer, is mixed with polysulfone in the stage of a membrane forming stock solution and the resulting mixture is molded to thereby impart hydrophilicity to a membrane and protect the membrane from stains (Patent Document 1). However, merely the addition of a hydrophilic component to a membrane forming stock solution cannot achieve a satisfactory deposition-preventing effect. Then, various improvements have been attempted. For example, a method in which a vinylpyrrolidone-type polymer as well as a polyglycol are added to a membrane forming stock solution to thereby increase the amount of the vinylpyrrolidone-type polymer present on the inner surface of a membrane (Patent Document 2) and a method in which a vinyl acetate group is provided on the surface of a membrane (Patent Document 3) are disclosed. In addition, a method in which a hydrophilic monomer is graft-polymerized onto the surface of a material (Non-Patent Document 1) is also disclosed. However, as a result of the extensive studies made by the present inventors, it is found that these methods are insufficient for developing anti-thrombotic properties. This is probably because attention is focused only on a hydrophilic polymer on the surface, adsorbed water in the polymer is not taken into consideration, and the physical configuration of the surface of a membrane is insufficient.

Further, in the case of an artificial kidney, after the completion of a blood dialytic therapy, a blood returning procedure in which a saline solution is allowed to pass through the artificial kidney and blood remaining in the artificial kidney and the blood circuit is returned into the body of a dialysis patient is carried out. However, blood that cannot be returned into the body is sometimes still remained in the artificial kidney, which is a phenomenon called "residual blood". The residual blood often occurs in an artificial kidney having poor anti-thrombotic properties, can cause anemia in a dialysis patient, and therefore should be avoided. Heretofore, various improvement methods have been proposed. As an invention for solving the problem of residual blood induced by the accumulation of blood in a zone that is the farthest from the center of axis of a main body case 10 (also referred to as "an outer peripheral part", hereinbelow) in header inner spaces 27 and 28 in a blood treatment apparatus 1 as shown in FIG. 2, for example, a method is proposed in which the clearance C between the outer peripheral surface of a hollow fiber membrane bundle 40 and the inner peripheral surface of each of headers 21 and 23 in each of partitioning wall edge faces 31 and 33 is reduced to thereby reduce the accumulation of blood (Patent Documents 4 and 5).

However, as a result of the repeated experiments made by the present inventors, it is found that the occurrence of residual blood is often observed even in an artificial kidney having a sufficiently small clearance C and therefore the above-mentioned inventions are insufficient for solving the problem of residual blood.

PATENT DOCUMENTS

Patent Document 1: Japanese Patent Publication No. 2-18695
Patent Document 2: Japanese Patent Laid-open Publication No. 6-165926
Patent Document 3: Japanese Patent Laid-open Publication No. 4-300636
Patent Document 4: Japanese Patent Laid-open Publication No. 63-9448
Patent Document 5: Japanese Patent Laid-open Publication No. 10-165777

NON-PATENT DOCUMENT

Non-Patent Document 1: Chiaki Yoshikawa et al. Macromolecules 2006, 39, 2284-2290

SUMMARY OF THE INVENTION

The present invention provides a medical material and a blood purification apparatus both having high anti-thrombotic properties and high safety.

The present inventors have made extensive studies for the purpose of solving the above-mentioned problems. As a result, it is found that a medical material and a hollow fiber membrane module both having high anti-thrombotic properties and high safety can be achieved by the following constitutions.

[1] A medical material having a hydrophilic copolymerization polymer present on a surface thereof which is to be in contact with blood (hereinbelow, also referred to as "a blood-contacting surface" for convenience), wherein particulate protuberances each having a particle diameter of 50 nm or more are present on the blood-contacting surface at a density of 3 particles/μm² or less and the relaxation time of adsorbed water in the hydrophilic copolymerization polymer is $2.5 \times 10^{-8}$ seconds or shorter and $5.0 \times 10^{-10}$ seconds or longer at −40° C.

It is preferred that a flexible layer is present on the blood-contacting surface when the material is in a moistened state and the flexible layer has a thickness of 7 nm or more.

It is preferred that the amount of the hydrophilic copolymerization polymer on the blood-contacting surface is 5 to 30% by weight inclusive.

As an embodiment of the medical material, a hollow fiber membrane can be mentioned, and a hollow fiber membrane module having a medical material incorporated therein can be used as an artificial kidney or the like.

As the polymer that constitutes the material, a polysulfone-type polymer can be used preferably.

[2] In the present invention, attention is focused on the overall improvement of anti-thrombotic properties of the hollow fiber membrane module, and it is found that a hollow fiber membrane module in which the hollow fiber membrane filling rate in a zone lying between an outermost periphery and a position located 1 mm apart from the outermost periphery toward an inner periphery in a module edge face part is 15% or more and the difference between the hollow fiber membrane filling rate in the zone and that in a center part is 40% or less enables the drastic improvement of the accumulation of blood in an outer peripheral part of the module.

[3] Another embodiment according to the present invention is examined more in detail with attention focused on the distribution and arrangement of hollow fiber membranes in the hollow fiber membrane module [2]. As a result, it is found that the improvement of accumulation of blood can be achieved more reliably by optimizing the constitution of the hollow fiber membrane module [2] as follows.

"A hollow fiber membrane module comprising: a hollow fiber membrane bundle; a main body case in which the hollow fiber membrane bundle is stored; partitioning walls which enable the hollow fiber membrane bundle to be held in a liquid-tight state at both ends of the main body case while keeping the hollow part edge faces in an opened state; and headers which are respectively attached both ends of the main body case and through which blood can be introduced and led out;

wherein the hollow fiber membrane filling rate in each of zones A to H, which are zones produced by dividing a zone lying between a position corresponding to the inner diameter of each of the headers and a position 1 mm apart from the aforementioned position toward the inner periphery into equal 8 parts equiangular with the center of axis of the main body case as its center in an edge face of each of the partitioning walls on a side facing each of the headers, falls within the range from 13 to 40%.

In the above-mentioned embodiment, the effect can become maximum by combining with a technique of arranging a hydrophilic copolymerization polymer having a relaxation time of adsorbed water of $2.5 \times 10^{-8}$ seconds or shorter and $5.0 \times 10^{-10}$ or longer at −40° C. on a blood-contacting surface of each of the hollow fiber membranes.

If particulate protuberances each having a particle diameter of 50 nm or more are present on the blood-contacting surface of each of the hollow fiber membranes at a density of more than 3 particles/μm², the blood accumulation effect cannot be developed greatly. Further, it is preferred that a flexible layer is present when the material is in a moistened state and the flexible layer has a thickness of 7 nm or more. It is also preferred that the amount of the hydrophilic copolymerization polymer on the blood-contacting surface of each of the hollow fiber membranes is 5 to 30% by weight inclusive.

The term "inner diameter of a header" as used herein refers to a value that is determined on a cross section taken at a position that overlaps an edge surface on a side facing a header of a partitioning wall. When the header diameter is altered on the cross section, the minimum value of the varied header diameters is defined as the "header inner diameter". When the header is provided with a ring-shaped elastic body such as an O-ring and the ring-shaped elastic body is in contact with the partitioning wall in the innermost periphery side thereof, the diameter at the position of the ring-shaped elastic body is defined as the "header inner diameter". The term "inner diameter of body part of a main body case" as used herein refers to a value that is determined on a cross section on which the inner diameter becomes minimum in the body part of the main body case.

The medical material according to the present invention has high anti-thrombotic properties and high safety. Particularly in an artificial kidney, when a hollow fiber membrane having high anti-thrombotic properties is used, the accumulation of blood in a zone that is the farthest from the center of the axis of a main body case in a header internal space is reduced and therefore it becomes possible to provide an artificial kidney having improved membrane performance and excellent residual blood performance.

DETAILED DESCRIPTION OF EMBODIMENTS OF THE INVENTION

Figure 1:
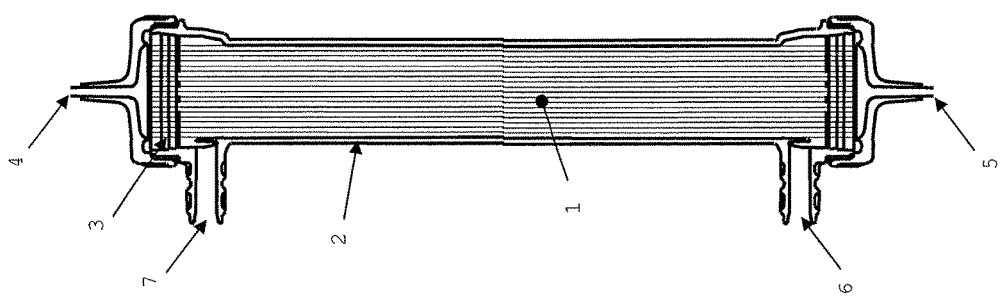
FIG. 1 shows a schematic cross sectional view of an embodiment of a blood treatment apparatus.

The invention of the present application has been accomplished on the basis of a finding that not only the physical structure but also the composition of the surface of a medical material are important for improving the anti-thrombotic properties of the medical material.

The medical material according to the invention of the present application contains a hydrophilic copolymerization polymer. The "hydrophilic" polymer in the hydrophilic copolymerization polymer refers to a polymer that contains at least one hydrophilic unit and can be dissolved in an amount of 0.1 g or more in 100 g of water at 20° C. That is, the hydrophilic copolymerization polymer is a polymer in which multiple monomer units are bound together by copolymerization, wherein at least one of the monomer units is a hydrophilic unit.

The medical material refers to a material to be used in a medical device that contacts with a body fluid, such as an artificial blood vessel, a catheter, a blood bag and a blood treatment apparatus. Examples of the blood treatment apparatus include an artificial kidney, an artificial liver, an artificial lung, a blood component adsorbent device and a plasma separator. As for the material, a polysulfone-type polymer such as polysulfone, polyethersulfone and polyarylate, polystyrene, polyethylene, polypropylene, polycarbonate, polyurethane, polyvinyl chloride, an acrylic resin such as polymethyl methacrylate, a fluororesin such as polyvinylidene fluoride, polyacrylonitrile, a polyester such as polyethylene terephthalate, and a polyamide can be used suitably. The material may be copolymerized with other monomer or may be modified, as long as the effect of the invention of the present application is not hindered. The preferred amount of the other copolymerization monomer is, but not limited to, 10% by weight or less.

When the hydrophilic polymer is present on the surface, a diffuse layer is formed on the surface. It is known that the deposition of a blood component can be inhibited by the excluded volume effect of the diffuse layer. The inventors of the present application found that the excluded volume effect of a diffuse layer containing a hydrophilic copolymerized copolymer is higher than a diffuse layer containing a hydrophilic homopolymer. This is probably because, for example in a homopolymer such as polyvinylpyrrolidone (PVP), the interaction between pyrrolidone rings is too strong, and therefore the intermolecular or intramolecular restraint becomes large and the turning radius of a molecular chain becomes small, resulted in insufficient development of the excluded volume effect of the diffuse layer.

In addition, as the result of the intensive studies made by the inventors of the present application, it is found that the deposition of a blood component is sometimes inhibited insufficient only by the excluded volume effect. It is found that adsorbed water of the hydrophilic copolymerization polymer is important for overcoming this problem. The term "adsorbed water" refers to water which interacts with the polymer and of which the mobility is lowered (i.e., has a longer relaxation time) compared with that of bulk water. In the invention of the present application, the relaxation time of the adsorbed water in the hydrophilic copolymerization polymer is preferably $2.5 \times 10^{-8}$ seconds or shorter, preferably $2.0 \times 10^{-8}$ seconds or shorter, and $5.0 \times 10^{-11}$ seconds or longer, preferably $8.0 \times 10^{-11}$ seconds or longer at −40° C. Although the reason why the relaxation time of the adsorbed water is considered to be important is unclear, since the relaxation time of the adsorbed water is about $10^{-9}$ to $10^{-10}$ seconds, it is considered that the influence of the surface of the membrane on a protein is small when the mobility of the adsorbed water in the protein is close to the mobility of the adsorbed water in the surface of the membrane.

The relaxation time of adsorbed water is a value obtained by a dielectric relaxation measurement, and is measured by cooling an aqueous hydrophilic copolymerization polymer solution having a concentration of 20% by weight or more to −40° C. The reason to cool to −40° C. is because bulk water is frozen at that temperature and therefore the measurement of adsorbed water can be performed easily. When a hydrophilic copolymerization polymer which cannot be dissolved at a concentration of 20% by weight or more is used, the measurement may be carried out using a suspended aqueous solution.

As for the hydrophilic copolymerization polymer having adsorbed water, a hydrophilic copolymerization polymer comprising a water-soluble unit and a hydrophobic unit is preferably used. The term "water-soluble unit" as used herein refers to a unit that is included within the range of the above-mentioned hydrophilic unit and has a high water solubility, and is a homopolymer of the above-mentioned unit which can be dissolved in an amount of 10 g or more in 100 g of water at 20° C. The "hydrophobic unit" as used herein refers to a unit that is a homopolymer of the above-mentioned unit and can be dissolved in an amount of less than 0.1 g in 100 g of water at 20° C. Examples of the water-soluble unit include vinylpyrrolidone, vinyl alcohol and ethylene glycol. Examples of the hydrophobic unit include vinylcaprolactam, propylene glycol, vinyl acetate, styrene, hydroxyethyl methacrylate and methyl methacrylate.

Although the reason why a hydrophilic copolymerization polymer comprising a water-soluble unit and a hydrophobic unit is proffered is unclear, it is assumed as follows: the interaction of a hydrophilic copolymerization polymer comprising only a water-soluble unit with a water molecule is too strong and therefore the mobility of adsorbed water is deteriorated, but a water molecule can be unstabilized when a hydrophobic unit is present and therefore the mobility of a water molecule present around a hydrophilic unit can be improved. If only a hydrophobic unit is contained, it is considered that the hydrophobic interaction becomes too strong and therefore the denaturation of a protein may be induced. For these reasons, with respect to the type of the copolymerization polymer, an alternating copolymerization polymer or a random copolymerization polymer can be used more suitably than a graft copolymerization polymer or a block copolymerization polymer. In this regard, a copolymerization polymer cannot be regarded as a block polymer, unless an average of 10 units each of which is one of the constituent units of the copolymerization polymer and is contained at a smaller composition ratio exists contiguously.

The (molar) ratio of the hydrophobic unit to all of units is preferably 0.3 to 0.7 inclusive. Particularly preferably used are a vinylpyrrolidone-vinylcaprolactam copolymerization polymer, a vinylpyrrolidone-vinyl acetate copolymerization polymer, a vinylpyrrolidone-hydroxyethyl methacrylate copolymerization polymer, vinylpyrrolidone-methyl methacrylate and ethylene glycol-polypropylene glycol. The copolymer may be of a two-component type or a multi-component type.

If the amount of the hydrophilic copolymerization polymer on the surface of the material is too small, the deposition of a blood component cannot be prevented. If the amount is too large, on the contrary, there is a concern about the elution of the hydrophilic copolymerization polymer. Further, in this case, the smoothness of the surface is lost and the surface becomes largely uneven. As a result, the number of particulate protuberances each having a particle diameter 50 nm or more is increased. Therefore, the amount of the hydrophilic copolymerization polymer present on the surface is preferably 5% by weight or more, more preferably 8% by weight or more, still more preferably 10% by weight or more, and is preferably 30% by weight or less, more preferably 20% by weight or less, still more preferably 15% by weight or less. When the material is used for an artificial kidney, when the hydrophobicity of the hollow fiber membrane is increased, water permeation performance is deteriorated and therefore the performance of the membrane is deteriorated. From this viewpoint, a too large amount of the hydrophilic copolymerization polymer is not preferred. It is also preferred that the hydrophilic copolymerization polymer exists only on the blood-contacting surface. Therefore, for the purpose of keeping high membrane performance, it is important that the ratio of the amount of the hydrophilic copolymerization polymer (also referred to as a "polymer amount", hereinbelow) present in an inner surface, which is a blood-contacting surface, of the hollow fiber membrane is larger than that on an outer surface of the hollow fiber membrane. The amount ratio of the hydrophilic copolymerization polymer in the inner surface is preferably larger by 1.1 times, preferably 2 times, more preferably 5 times or more, than that in the outer surface. The ratio of the amount of the hydrophilic copolymerization polymer in the outer surface is less than 10% by weight, preferably less than 5% by weight.

The reason why it is necessary to provide the flexible layer on the blood-contacting surface when the material is in a moistened state is assumed as follows: platelets and blood cells are less likely to get closer to the material and are less likely to be deposited or activated when the flexible layer that constitutes the material becomes thicker. If the flexible layer is too thick, on the contrary, a protein might be trapped by the flexible layer. For these reasons, the thickness of the flexible layer is preferably 5 nm or more, more preferably 7 nm or more, and is preferably 30 nm or less, more preferably 20 nm or less, still more preferably 15 nm or less. The moistened state refers to a state in which the water content is 65% by weight or more.

Figure 3:
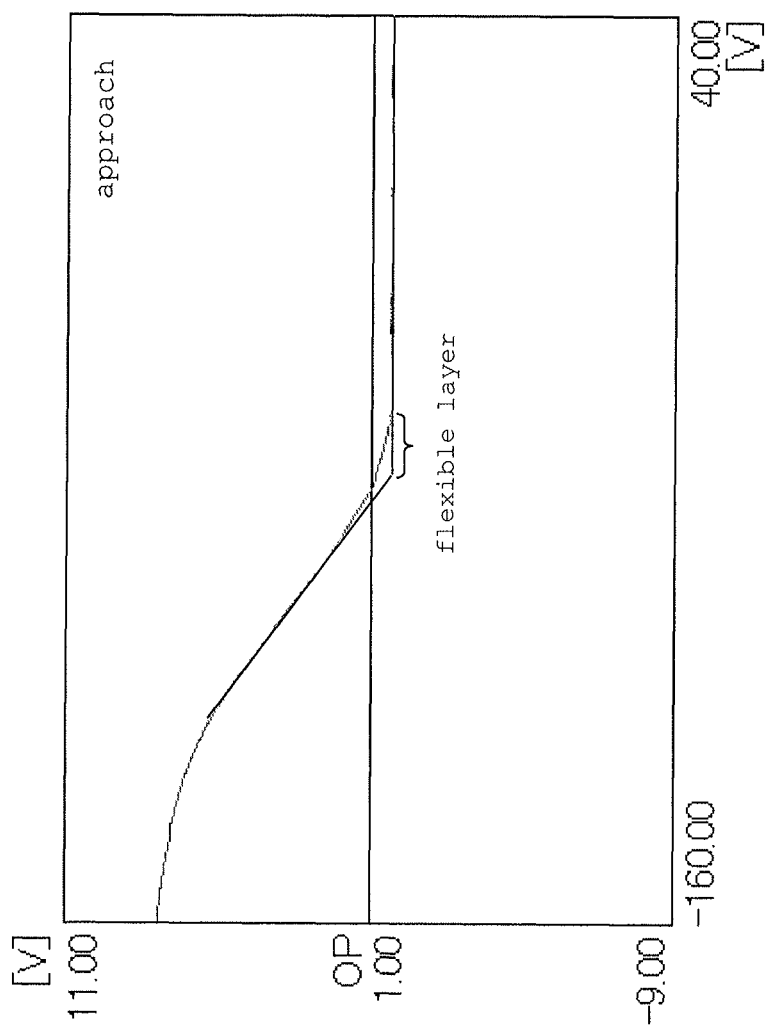
FIG. 3 shows a curve illustrating the relationship between the force acting on a cantilever and the displacement amount of the cantilever in a force curve measurement using an atomic force microscope.

The thickness of the flexible layer on the surface of a separation membrane functional layer in a moistened state can be calculated by a force curve measurement using an atomic force microscope. A force curve is expressed by a displacement amount of a cantilever on a horizontal axis wherein the force acting on the cantilever is plotted on the vertical axis. Until a shorter hand of the cantilever is in contact with the surface of the functional layer, the force curve is shifted in parallel with the x-axis. After the cantilever contacts with the surface of the functional layer, when there exists the flexible layer, a curved non-linear part appears. Thereafter, a linear relationship is obtained between the displacement force of the cantilever and the force of the cantilever. The thickness of the flexible layer is defined as a distance from an intersection point between an extended line of a part that becomes linear after the contact of the shorter hand of the cantilever with the surface and an extension of a line that is shifted in parallel with the x-axis before the contact of the shorter hand of the cantilever with the surface to a point at which the shorter hand of the cantilever contacts with the surface (FIG. 3).

Examples of the method for producing the material having a surface of the flexible layer thickness include: a method of coating the hydrophilic copolymerization polymer onto the surface of the material; a method of immobilizing the hydrophilic copolymerization polymer onto the surface of the material by cross-linking; and a method of blending the hydrophilic copolymerization polymer to a polymer stock solution for forming the medical material and molding the resulting blend.

When a post-treatment is carried out using the hydrophilic copolymerization polymer by coating or the like, the concentration of the hydrophilic polymer in the coating solution, the time of contact and the temperature employed for the coating affect the (surface) amount of the polymer coated or the like and so on. For example, the coating is carried out using a solution of a vinylpyrrolidone-vinylcaprolactam copolymerization polymer, a vinylpyrrolidone-vinyl acetate copolymerization polymer or ethylene glycol-polypropylene glycol, the concentration in the aqueous solution is preferably 1 to 5000 ppm, the contact time is preferably 10 seconds or longer, and the temperature is preferably 10 to 80° C. In the case where the coating is carried out in a continuous mode, not in a batch mode, the aqueous coating solution can be coated more uniformly when the flow rate of the aqueous coating solution is higher. However, the flow rate is too rapid, a sufficient amount cannot be coated. Therefore, the flow rate is preferably falls within the range from 200 to 1000 mL/min. When the coating is carried out in this range, a uniform coating can be achieved. A care should be taken not to form an uneven coating, unless protruding objects may be formed.

When the hollow fiber membrane is coated, it is preferred that the hydrophilic copolymerization polymer is applied onto only the blood-contacting surface of the hollow fiber membrane. In the case of an artificial kidney or the like, the inside of the hollow fiber membrane corresponds to the blood-contacting surface. Therefore, a method in which a difference in pressure is produced from the inside of the hollow fiber membrane toward the outside of the hollow fiber membrane to coat the hollow fiber membrane with the hydrophilic copolymerization polymer is preferred, since the hydrophilic copolymerization polymer can be introduced efficiently onto the inner surface of the hollow fiber membrane. The difference in pressure is preferably 10 mmHg or more, more preferably 50 mmHg or more, between the coating solution inlet side (the inside of the hollow fiber) and the coating solution outlet side (the outside of the hollow fiber) in the hollow fiber membrane module. Further, a procedure for allowing a gas (e.g., compressed air), water, an aqueous solution that does not contain the hydrophilic copolymerization polymer or the like to flow in a direction opposite to the direction of the coating of the hydrophilic polymer (i.e., in a direction from the outside of the hollow fiber toward the inside of the hollow fiber) is a particularly preferred technique, since the procedure enables the concentration of the polymer that is one-layer-coated only on the inner surface. The flow rate of a gas (e.g., compressed air) to be flow from the outside of the hollow fiber toward the inside of the follow fiber is preferably 70 NL/min or less, more preferably 50 NL/min or less, and the gas is preferably allowed to flow for 10 minutes or shorter. In the case of water or an aqueous solution, the water or the aqueous solution is preferably allowed to flow at a flow rate of 1 L/min or less, more preferably 0.5 L/min or less, preferably for 1 minute or shorter. An operation of pressurizing the outside of the hollow fiber membrane to blow a gas into the inside of the hollow fiber membrane intermittently is preferred, since an excess portion of the polymer can get brown and can be removed and therefore uniform coating can be achieved. The term "intermittently" as used herein refers to a matter that the increase and decrease of the flow rate of the gas is altered repeatedly while varying a pressure, and it is preferred to repeat the blowing at a highest pressure and the blowing at a lowest pressure within a certain fluctuation range. The ratio of the largest flow rate to the smallest flow rate or the ratio of the highest pressure to the lowest pressure is preferably 1.5 times or more, more preferably 2 times or more. The smallest flow rate of the gas to be flown through the inside of the hollow fiber membrane is preferably 0.1

NL/min or more and 10 NL/min or less, and the largest flow rate is preferably 0.15 NL/min or more and 30 NL/min or less.

When only the coating is performed, the hydrophilic copolymerization polymer may be eluted from the material as used. Therefore, it is preferred to perform cross-linking with heat or a radioactive ray after the coating. However, if the cross-linking is performed merely by the irradiation with a radioactive ray, the state of water adsorbed onto the hydrophilic copolymerization polymer may be altered. Then, γ-ray or electron beam is employed as the radioactive ray. When γ-ray is employed, the preferred dose range is 2500000 to 10000000 Ci or more, preferably 3000000 to 7500000 Ci. When electron beam is employed, the acceleration voltage is 5 MeV or more, preferably 10 MeV or more. The preferred dose of irradiation is 5 to 50 kGy, preferably 10 to 35 kGy, and the preferred temperature for irradiation is 10 to 60° C., preferably 20 to 50° C. It is also preferred to perform the irradiation with the radioactive ray within two weeks, preferably one week, after the coating. After the coating, it is desirable that the coated product is stored at 0° C. to 60° C., preferably 5 to 50° C. or lower and then is immediately subjected to a cross-linking treatment with the radioactive ray. When heating is required for convenience of the process, it is desirable to carry out the heating within a short time. Specifically, when the heating is carried out at 100° C. or higher, the time for the heating is preferably 10 minutes or shorter. This is because the state of the polymer existing on the surface may be altered after the coating due to the molecular motion of the polymer or the like. Further, if an ion is present, the state of adsorbed water is also altered. Therefore, it is preferred that any inorganic ion such as a sodium ion and a calcium ion is not present during the irradiation with the radioactive ray. Specifically, when the material is in a moistened state, the concentration of ions in water is preferably 1000 ppm or less, more preferably 100 ppm or less. The amount of water to be contained in the material is 6 times or less, preferably 4 times or less, the dried weight of the material. The material may be irradiated with the radioactive ray in a dried state (i.e., a state in which the material is not moistened with water), but the amount of water to be contained in the material is preferably 0.05 time or more the dried weight of the material.

For the purpose of controlling the cross-linking, an antioxidant agent, i.e., a radical trap agent as used in the present invention, may be used. The term "radical trap agent" as used herein refers to a molecule that has a property of being likely to donate an electron to another molecule. Examples of the radical trap agent include, but not limited to: a water-soluble vitamin such as vitamin C; a polyphenol; an alcohol such as methanol, ethanol, propanol, ethylene glycol, propylene glycol and glycerin; a saccharide such as glucose, galactose, mannose and trehalose; an inorganic salt such as sodium hydrosulfite, sodium pyrosulfite and sodium dithionate; uric acid; cysteine and glutathione. When an inorganic salt is used, a careful attention should be paid to the upper limit of the concentration to be added, as stated above. These radical trap agents may be used singly, or a mixture of two or more of the radical trap agents may be used. The radical trap agent is preferably added in the form of an aqueous solution. In this case, the oxygen concentration in the aqueous solution is preferably 10 mg/L or less, more preferably 5 mg/L or less, since oxygen dissolved in the aqueous solution or oxygen in the atmosphere can accelerate oxidative decomposition. The oxygen concentration in the gas to be contacted with the separation membrane upon the irradiation with the radioactive ray is preferably 5% or less, more preferably 3% or less. Among the above-mentioned radical trap agents, a monohydric alcohol such as ethanol, propanol, butanol, pentanol and hexanol is preferably used. When ethanol, n-propanol or 2-propanol is used, the concentration in the aqueous solution is preferably 0.01% by weight or more and 10% by weight or less, more preferably 0.05% by weight or more and 1% by weight or less. When propylene glycol or glycerin is used, the concentration is preferably 0.1% by weight or more and 90% by weight or less, more preferably 0.5% by weight or more and 70% by weight or less.

Next, the method for blending the hydrophilic copolymerization polymer to a polymer stock solution for medical material molding purposes and molding the resulting blend is described. For example, for a hollow fiber membrane, a method for spinning a membrane forming stock solution comprising a polysulfone-type polymer and the hydrophilic copolymerization polymer is employed. In this case, a third component such as PVP may be added. Further, the hydrophilic copolymerization polymer may be added to a core injection solution during the formation of a membrane of the hollow fibers. A method in which a polysulfone-type hollow fiber membrane is molded and then the hydrophilic copolymerization polymer is introduced into the surface of the hollow fiber membrane by a post-treatment is also one of preferred methods.

When the hydrophilic copolymerization polymer is added to the membrane forming stock solution, the spinning conditions are as follows: the mold temperature preferably ranges from 30 to 60° C., the temperature of a dry unit preferably ranges from 20 to 50° C., and the relative humidity preferably ranges from 70 to 95% RH. The temperature of the dry unit is preferably lower than the mold temperature, more preferably lower by 10° C. or more than the mold temperature. The length of the dry unit is preferably 10 to 100 cm. The mold temperature is preferably the same as the storage temperature for the membrane forming stock solution or lower. This is because the structure of a polymer is established with a thermal history left therein when the temperature at a discharge part is increased, which is undesirable because distortion may remain in molecules of the polymer after the molding.

For the purpose of allowing the hydrophilic copolymerization polymer to exist in the inner surface of the hollow fiber membrane in a larger amount than that in the outer surface of the hollow fiber membrane, it is preferred to use a mixed solution of a good solvent and a poor solvent for the polysulfone-type polymer in a coagulating bath. Examples of the good solvent include N,N'-dimethylacetamide (DMAc) and N-methylpyrrolidone, and examples of the poor solvent include water and an alcohol. The concentration of the good solvent to be employed is preferably 10% by weight or more, more preferably 15% by weight or more, and is preferably 30% by weight or less, more preferably 25% by weight or less.

A method in which the outer surface of the hollow fiber membrane is washed with water, an aqueous DMAc solution or the like in a spinning step to reduce the amount of the hydrophilic copolymerization polymer in the outer surface of the hollow fiber membrane is preferred.

When the hydrophilic copolymerization polymer is added to the core injection solution, the content ratio of the core injection solution, the temperature of the core injection solution, the composition of the membrane forming stock solution and the like affect the amount of the hydrophilic copolymerization polymer in the surface of the hollow fiber membrane. For example, when a vinylpyrrolidone-vinyl acetate copolymerization polymer is added to the core injection solution and then the resulting core injection solution is added to a membrane forming stock solution comprising polysulfone and PVP, the amount to be added to the core injection solution is preferably 5 to 30% by weight, the temperature of the core injection solution is preferably 10 to 60° C., and the membrane forming stock solution preferably has such a composition in which the polysulfone concentration is 14 to 25% by weight and the PVP concentration is 2 to 10% by weight. For improving the remainability of the vinylpyrrolidone-vinyl acetate copolymerization polymer on the surface of the membrane, polysulfone preferably has a smaller weight average molecular weight and polysulfone having a weight average molecular weight of 100000 or less, preferably 50000 or less, can be used suitably.

In the present invention, it is found that the deposition of a blood component cannot be sometimes controlled satisfactorily merely by optimizing the surface composition of the material. Then, the physical structure of the surface of the material is examined and attention is particularly focused on particulate protuberances on the surface. The particulate protuberances are formed from a polymer that mainly constitutes the material. In the invention of the present application, it is found that the content ratio of particulate protuberances particularly each having a particle size (particle diameter) of 50 nm or more present on the inner surface of the membrane is 3 particles/$\mu m^2$ or less, preferably 2 particles/$\mu m^2$ or less, more preferably 1 particle/$\mu m^2$ or less. When each of the particulate protuberances is not circular and is oval, the particle diameter is defined as the major axis, i.e., the longest diameter. When the protuberances have irregular shapes and it is impossible to determine the major axis, the diameter can be determined by calculating the area of each of the protuberances and then converting into its equivalent in a circular shape (i.e., an equivalent circle diameter). That is, when many particulate protuberances are present, the deposition of a blood cell component is induced. The reason for this is assumed that platelets can be deposited easily due to the physical stimuli from the protuberances on the cell membrane or the like. If the amount of the hydrophilic copolymerization polymer on the surface is increased, protuberances may be formed easily. In addition, if the coating amount of the hydrophilic copolymerization polymer on the surface of the material is uneven, areas in which the amount of the hydrophilic copolymerization polymer is large occur on the surface and therefore protuberances may be formed easily. When the medical material is a hollow fiber membrane for a blood purification apparatus, if many protuberances are present on the surface of the membrane, the flow on the surface of the membrane is disturbed and therefore the film resistance of the membrane is decreased. From the viewpoint of the membrane performance, it is preferred that the abundance ratio of the particulate protuberances is high and is preferably 0.1 particle/$\mu m^2$ or more, more preferably 0.2 particle/$\mu m^2$ or more. In the case of a blood purification apparatus, since the number of contacts of platelets with the material is restricted due to the flow of blood, it is considered that the influence of protuberances is smaller compared with a medical material that is indwelled in the body.

The confirmation on the existence of the particulate protuberances on the surface of the material is carried out by the magnifying observation at a magnification of 50000 times on a scanning electron microscope.

The development of the particulate protuberances on the surface is affected by the state of dispersion of the polymer in the membrane forming stock solution, the state of phase separation during spinning and the like. Therefore, for reducing the particulate protuberances on the surface of the membrane, it is very preferred that a hydrophilic polymer having good compatibility with the polysulfone-type polymer is added to the membrane forming stock solution. Specific examples of the hydrophilic polymer include PVP, polyethylene glycol, polyvinyl alcohol and derivatives thereof.

In the membrane forming stock solution, the concentration of the polysulfone-type polymer is preferably 14 to 25% by weight, more preferably 15 to 20% by weight, and the concentration of the hydrophilic polymer is preferably 2 to 10% by weight, more preferably 3 to 9% by weight. The ratio of the weight of the hydrophilic polymer relative to the total weight of all of the polymers contained in the membrane forming stock solution is preferably 0.15 to 0.35 time, more preferably 0.2 to 0.3 times. The polysulfone-type polymer preferably has a weight average molecular weight of 30000 or more, and ratio of the weight average molecular weight of the hydrophilic polymer is preferably larger by 15 to 40 times, more preferably 20 to 35 times, than that of the polysulfone-type polymer.

It is preferred to agitate the membrane forming stock solution at a high agitation speed, since the state of dispersion of the hydrophilic polymer and the polysulfone-type polymer becomes uniform. The speed of an impeller is preferably 30 rpm or more, more preferably 50 rpm or more. If the dissolution temperature is low, uniform microdispersion cannot be achieved. If the dissolution temperature is too high, the decomposition of the polymer may be caused. Therefore, the dissolution temperature is preferably 60° C. or higher, more preferably 80° C. or higher, and is preferably 120° C. or lower, more preferably 100° C. or lower. Over time, the microphase separation begins to start in the membrane forming stock solution and the hydrophilic polymer cannot be microdispersed uniformly. Therefore, it is preferred to spin the solution within 80 hours after the dissolution. The storage temperature after the dissolution is preferably 45° C. or higher, more preferably 60° C. or higher, and is preferably 90° C. or lower, more preferably 80° C. or lower.

With respect to the spinning conditions, the mold temperature is preferably 30 to 60° C., the temperature of the dry unit is preferably 20 to 50° C., the relative humidity is preferably 70 to 95% RH. The temperature of the dry unit is preferably lower, preferably by 10° C. or more, than the mold temperature. The length of the dry unit is preferably 10 to 100 cm. The mold temperature is preferably equal to or lower than the storage temperature for the membrane forming stock solution. For the coagulating bath, a mixed solution of a good solvent and a poor solvent for the polysulfone-type polymer is preferably used. Examples of the good solvent include DMAc and N-methylpyrrolidone. Examples of the poor solvent include water and an alcohol. The concentration of the good solvent is 10% by weight or more, preferably 15 to 30% by weight inclusive, and preferably 25% by weight or less. The temperature of the coagulating bath is preferably 20° C. or higher and 60° C. or lower.

If the hollow fiber membrane is dried after the formation thereof, particulate protuberances are likely to be produced and therefore a careful attention should be paid. That is, it is considered that particulate protuberances are formed when the membrane is shrunk upon being dried. It is preferred to employ a rapid drying rate, since the membrane can be dried before the formation of the protuberances and therefore the number of the protuberances on the surface of the membrane can be reduced. If a slow drying rate is employed, on the other hand, the protuberances are likely to be formed, since there is a time for causing the change in configuration of the surface of the membrane. Therefore, the drying temperature is preferably 200° C. or lower, more preferably 170° C. or lower, still more preferably 150° C. or lower, and is preferably 90° C. or higher, more preferably 100° C. or higher, still more preferably 110° C. or higher. It is also preferred to apply a certain degree of tensile force to the hollow fiber membrane during drying, from the viewpoint of the reduction in protuberances formed. The tensile force to be applied immediately before the drying step is preferably 15 g/mm$^2$ or more, more preferably 50 g/mm$^2$ or more. If the tensile force is too high, the performance of the membrane may be altered. Therefore, the tensile force is preferably 500 g/mm$^2$ or less, more preferably 250 g/mm$^2$ or less.

The hollow fiber membrane module has multiple pieces of the hollow fiber membranes incorporated therein. If such a drift of blood flow that blood flows in a larger amount in some of the hollow fiber membranes occurs, even if the performance of the individual hollow fiber membranes is high, high overall performance of the module cannot be achieved. Further, if such the drift of blood flow occurs, a problem of so-called "occurrence of residual blood" may arise. The term "occurrence of residual blood" as used herein refers to such a phenomenon that blood remains in the module when blood in a circuit or a module is returned into a body after a dialytic therapy. The occurrence of residual blood in clinical practice is induced by a cause other than the drift of blood flow, e.g., the deposition of platelets or the like onto the membrane, and is considered as a measure for the overall anti-thrombotic properties of the hollow fiber membrane module.

In the present invention, it is found that the distribution of the hollow fiber membranes on the transverse section of the hollow fiber membrane module is also a critical factor for solving the above-mentioned problem.

That is, the filling rate in a zone lying between the outermost periphery of the edge face part of the hollow fiber membrane module and a position located 1 mm apart from the outermost periphery toward the inner periphery is preferably 15 or more, more preferably 20% or more. If the filling rate exceeds 40%, the opening of the hollow fiber membrane 41 may be closed with a contact surface 25 that contacts with a partitioning wall of a header. The outermost periphery of the edge face part corresponds to the inner peripheral surface of a case of the module in which the hollow fiber membranes are stored. When the diameter of the inner peripheral surface of the header is smaller than that of the case, since a zone lying between the case inner peripheral surface and a position 1 mm apart from the inner peripheral surface toward the inner periphery is filled with a ring-shaped elastic body or the like, the hollow fiber membranes are not arranged generally. Therefore, in this case, a header inner peripheral surface is deemed as a case inner peripheral surface. An edge face part is a face on which edge parts of hollow fiber membranes exist, and refers to an outer partitioning wall edge face part when the edge parts of the hollow fiber membranes are fixed by means of a partitioning wall at the edge part of the casing. In the present invention, it is preferred that the difference between the hollow fiber membrane filling rate in a zone lying between the outermost periphery and a position 1 mm apart from the outermost periphery (an outermost periphery zone) and the hollow fiber membrane filling rate in the center part is within 40%, preferably within 30%. The term "center part" as used herein refers to a cylindrical internal zone having a radius that is half of the distance between the center point of the case and the inner peripheral surface of the case. When the radius of the header inner peripheral surface is smaller than that of the case inner peripheral surface as mentioned above, the radius of the center part may be half of the distance between the case center point and the header inner peripheral surface.

With respect to the overall filling rate (a filling rate in a body part), the lower limit is limit is preferably 53% or more, more preferably 55% or more, still more preferably 57% or more, and the upper limit is preferably 64% or less, more preferably 62% or less, still more preferably 60% or less.

The position at which the filling rate is to be measured may be any position other than a position in which a potting material is filled (e.g., a module end). Details of the method for measuring the filling rate are as mentioned in the section "Examples" below.

If the difference between the fiber filling rate in the outermost peripheral zone and the filling rate in the center part is too large, blood is likely to flow in fibers located in the center part and therefore blood is likely to be accumulated in the outer peripheral part. As a result, the activation of blood may be induced or the module may not exhibit its performance sufficiently.

Further, it is more preferred that the hollow fiber membrane filling rate in each of zones A to H, which are zones produced by dividing a zone lying between a position corresponding to the inner diameter of each of the headers and a position 1 mm apart from the aforementioned position toward the inner periphery into equal 8 parts equiangular with the center of axis of the main body case as its center, falls within the range from 13 to 40%. When the filling rate is defined in each of these zones, good blood flow can be achieved if the difference between the hollow fiber membrane filling rate in the zone lying between the outermost periphery and a position 1 mm apart from the outermost periphery and that in the center part is 50% or less.

For the purpose of arranging the fibers in the outermost periphery, a method in which the hollow fiber membrane bundle is inserted into a case and is then blown with air from the edge face of the case to scatter the fibers forcibly, a method in which a potting material is injected through a nozzle located on a blood side, and the like is preferably employed. As for the shape of the hollow fiber, a crimp structure is preferred. Specifically, the wave height is preferably 0.1 to 1.5 mm, more preferably 0.1 to 1.0 mm, still more preferably 0.1 to 0.5 mm, and the wave length is preferably 5 to 30 mm, more preferably 5 to 20 mm, still more preferably 5 to 10 mm.

The term "amplitude" in a crimp of the hollow fiber membrane refers to a width of a wave of the waving hollow fiber membrane (i.e., half of a distance between the largest value and a smallest value on a y-axis of one wave (i.e., wave height)). The term "pitch" is also refers to a "wave length", and refers to a distance between the peak of a wave (i.e., a position at which the width of a wave becomes maximum on a y-axis in one wave length) and the peak of a next wave.

The embodiment according to item [3] mentioned above according to the present invention is described with reference to drawings.

Figure 2:
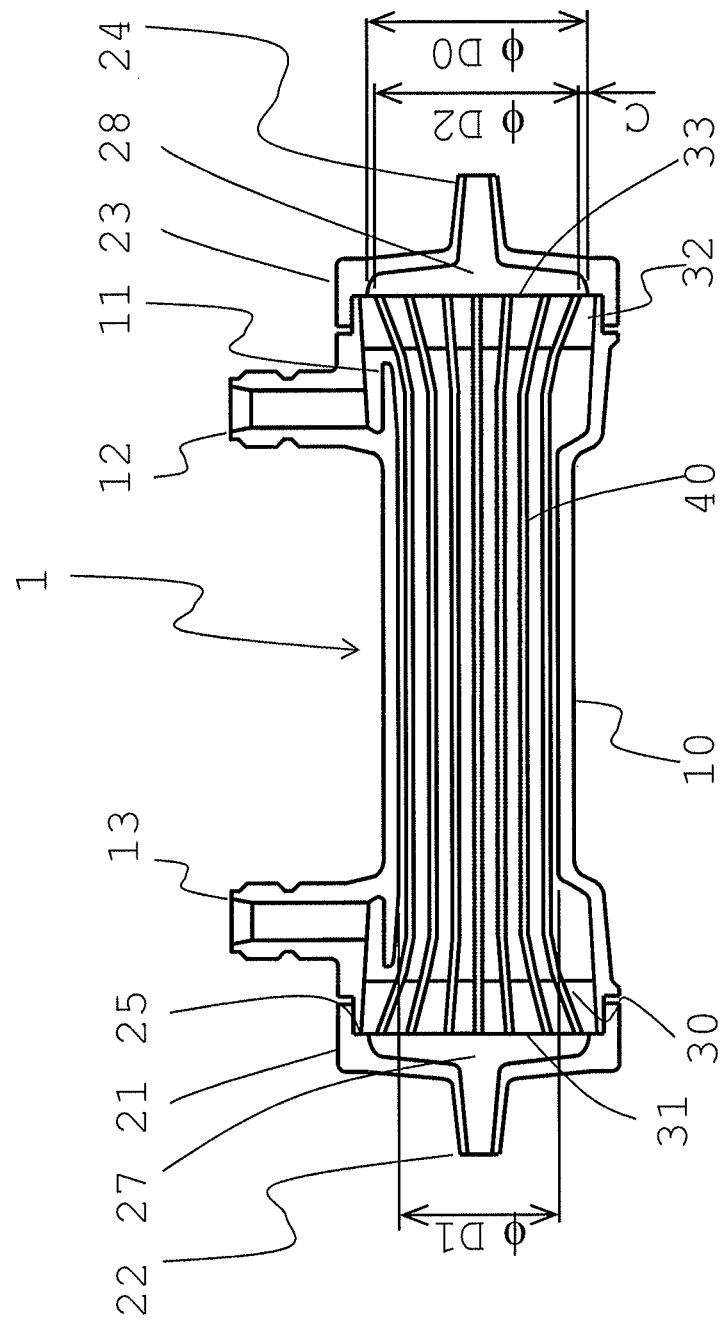
FIG. 2 shows a schematic cross sectional view illustrating an embodiment of a blood treatment apparatus more in detail.
Figure 4:
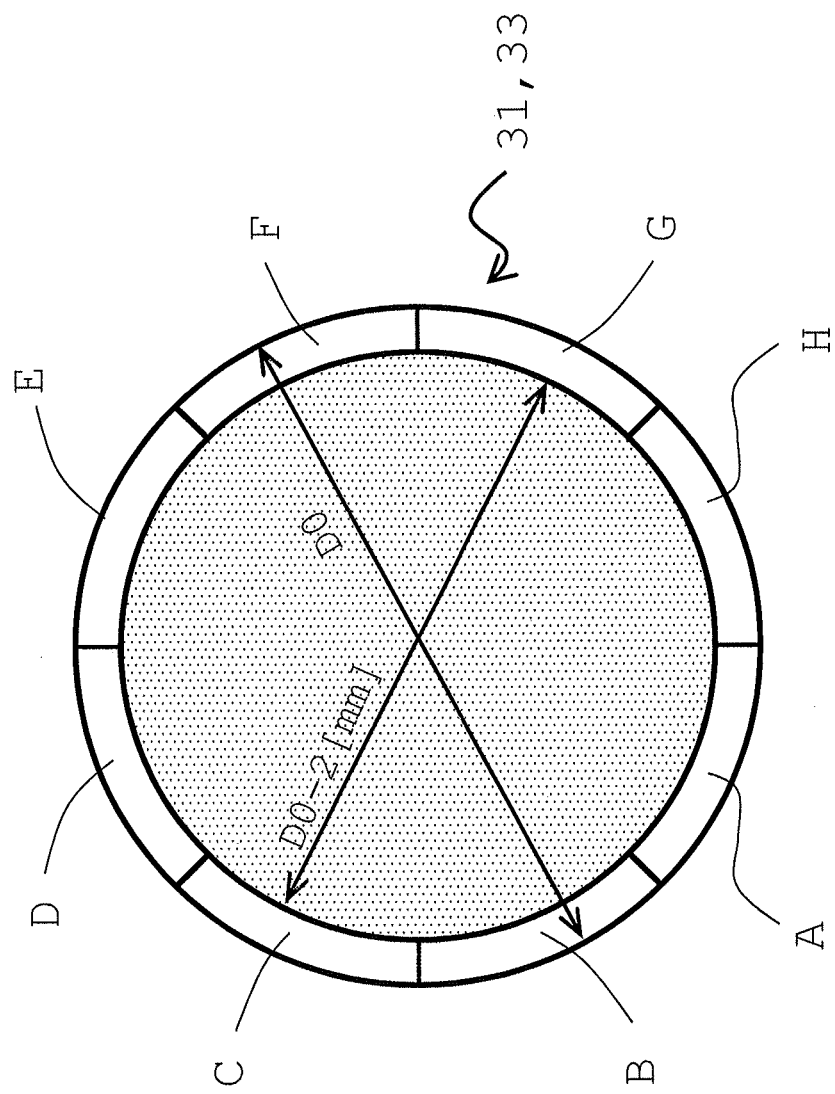
FIG. 4 shows a schematic view of a zone of which the filling rate is to be measured at an partitioning wall edge face.
Figure 5:
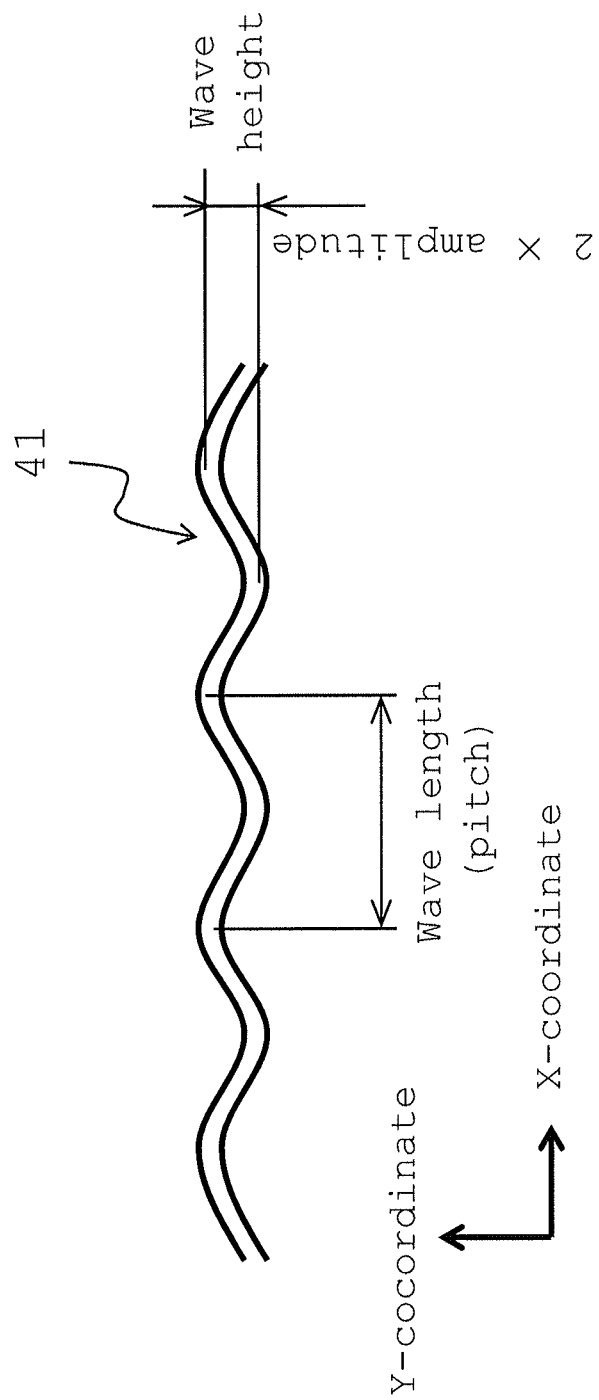
FIG. 5 shows a schematic view of an embodiment of a crimp structure of a hollow fiber membrane.

FIG. 2 is a vertical cross sectional view that illustrates one embodiment of a blood treatment apparatus 1 in detail. FIG. 4 is a schematic view that illustrates a zone in which the filling rate is to be measured in an edge face 31 on a side facing a header for a partitioning wall. FIG. 5 is a schematic view that illustrates the shape of a crimp formed in the hollow fiber membrane 41.

In FIG. 2, one embodiment of a blood treatment apparatus 1 is illustrated, which is equipped with: a hollow fiber membrane bundle 40 which is produced by binding up multiple polysulfone-type hollow fiber membranes and through which blood flows; a main body case 10 in which the hollow fiber membrane bundle is stored; partitioning walls 30 and 32 which enables the hollow fiber membrane bundle 40 to be held in a liquid-tight state at both ends of the main body case 10 while keeping the edge faces of the hollow fiber membranes in an opened state; a blood inlet header 21 which is attached to one end of the main body case 10 and through which blood is introduced into the hollow fiber membrane bundle 40; and a blood outlet header 23 which is attached to the other end of the main body case 10 and through which blood is led out.

In the blood treatment apparatus, a dialyzate inlet port 12 is formed at one end of the outer peripheral surface of the main body case 10, a dialyzate outlet port 13 is formed at the other end of the outer peripheral surface of the main body case 10, and a baffle 11 which can arrange the flow of a dialyzate is formed immediately beneath each of the ports 12 and 13 in such a manner that the baffle 11 extends from the body part of the main body case 10 and a distance is provided between the tip of the baffle 11 and each of the partitioning walls 30 and 32. The main body case 10 and each of the headers 21 and 23 are joined so that the headers are pressed against the partitioning wall edge faces 31 and 33, thereby forming header internal spaces 27 and 28.

The present inventors have found that the filling rate of the hollow fiber membrane 41 in a zone lying between a position corresponding to the inner diameter of each of the headers and a position 1 mm apart from the aforementioned position toward the inner periphery in the partitioning wall edge faces 31 and 33 is a critical factor for improving the occurrence of residual blood in the blood treatment apparatus. That is, it is found that, if the number of the hollow fiber membrane 41 is small (in other words, if the filling rate of the hollow fiber membrane is low) in the zone, since the amount of blood flowing into the hollow fiber membrane 41 in the zone is reduced, the flow rate of blood in the outer peripheral parts of the header internal spaces 27 and 28 is reduced and the viscosity of blood (which is a non-Newtonian fluid) is increased, resulted in the formation of blood-accumulated parts. Particularly in a blood treatment apparatus 1 in which the filling rate of the hollow fiber membrane 41 in each of the partitioning wall edge faces 31 and 33 is lower than that in the body part of the main body case 10, such a tendency is observed remarkably that there occurs the uneven distribution in the hollow fiber membrane bundle 40 and a zone having a lower filling rate is likely to be formed locally.

Then, in another embodiment of the blood treatment apparatus according to the present invention, in each of zones A to H, which are zones produced by dividing a zone lying between a position corresponding to the inner diameter of each of the headers and a position 1 mm apart from the aforementioned position toward the inner periphery into equal 8 parts equiangular with the center of axis of the main body case as its center in each of the edge faces 31 and 33 of each of the partitioning wall 30 and 32 on a side facing each of the headers 21 and 23 as shown in FIG. 4, the filling rate of the hollow fiber membranes is set at 13 to 40%. The upper limit of the filling rate of the hollow fiber membranes is preferably 35% or less. The lower limit is preferably 15% or more, more preferably 19% or more. When the filling rate in each of the zones A to H is set at 13% or more, the decrease in the flow rate of blood in the outer peripheral parts of the header internal spaces 27 and 28 can be prevented and the occurrence of the accumulation of blood can also be prevented. If the filling rate is lower than 13%, since blood cannot flow into the insides of the hollow fiber membrane 41 easily even if the clearance C between the outer periphery of the hollow fiber membrane bundle 40 and the inner periphery of each of the headers 21 and 23 is reduced, blood is likely to be accumulated, resulted in the induction of the activation of blood and the occurrence of residual blood. If the filling rate excesses 40%, the probability of blocking off the openings of the hollow fiber membrane 41 by a contact surface 25 that contacts with each of the partitioning walls of the headers is increased.

The hollow fiber membrane filling rate in each of the edge faces 31 and 33 of the partitioning walls 30 and 32 on a side facing each of the headers 21 and 23 can be set as mentioned above in the following manner, for example. Prior to the formation of the partitioning walls 30 and 32, the hollow fiber membrane bundle is inserted into the main body case 10 in such a manner that the end parts of the hollow fiber membrane bundle are protruded outside of the main body case 10, and then the end part of each of the hollow fiber membranes is sealed. In this regard, it is preferred that the fiber bundles is arranged by, for example, sandwiching the outer peripheral parts of the protruded parts by opposed two plates (referred to as "cover plates", hereinbelow) each having a semicircular cutout section, so that adjacent hollow fiber membranes can contact with each other lightly simultaneously with the sealing of the hollow parts. The diameter of the cutout section is determined properly, depending on the inner diameter of the body part of the main body case 10 and the header inner diameter. When the diameter of the cutout section is slightly smaller than the case inner diameter or the header inner diameter, adjacent hollow fiber membranes can contact with each other lightly simultaneously with the sealing of the hollow parts, as mentioned above. If the diameter of the cutout section is smaller than the case inner diameter or the header inner diameter and the difference between the diameter of the cutout section and each of the case inner diameter and the header inner diameter is large, it is difficult to set the filling rate of the hollow fiber membranes in each of the zones A to H at 13% or more.

The hollow fiber membrane bundle 40 is preferably arranged in such a manner that the outer diameter of the hollow fiber membrane bundle 40 is increased gradually from the tip part of the baffle 11 toward the outer end of the main body case 10. For this purpose, it is preferred to air-blow the edge surface of the hollow fiber membrane bundle. It is also preferred that, in the edge faces 31, 33 of the partitioning walls 30 and 32 on a side opposed to the header, the clearance C between the outer periphery of the hollow fiber membrane bundle 40 and the inner periphery of each of the headers 21 and 23 becomes 0.3 to 0.6 mm. By setting the value of the clearance C at any value falling within the above-mentioned range, it becomes possible to further reduce the accumulation of blood in the outer peripheral parts of the header internal spaces 27 and 28 and further reduce the possibility of the occurrence of residual blood while preventing the action of the headers 21 and 23 on the openings of the hollow fiber membranes in such a manner that the headers 21 and 23 block off the openings of the hollow fiber membranes. The proper range of the clearance C can be selected properly depending on the shape of the hollow fiber membrane bundle and the filling rates, and is therefore not limited to the above-mentioned range.

The ratio of the inner diameter D0 of each of the headers 21 and 23 to the body part inner diameter D1 of the main body case 10 (i.e., (D0/D1)) is preferably 1.05 to 1.25, more preferably 1.15 to 1.25. If the ratio is smaller than 1.05, it becomes difficult for a dialyzate to flow into the center part of the hollow fiber membrane bundle 40 easily and therefore bubble removability upon priming tends to be deteriorated. Further, the efficiency of the diffusion of a low-molecular-weight substance such as urea from blood into the dialyzate is reduced slightly, and therefore the dialysis performance such as urea clearance tends to be deteriorated. If the ratio is larger than 1.25, it becomes difficult to keep the hollow fiber membrane filling rate in each of the zones A to H at 13% or more.

Each of the hollow fiber membranes preferably has a crimp structure, as shown in FIG. 5. The preferred ranges for the wave height and the wave length are as mentioned above. If the wave height is smaller than 0.1 mm, it becomes difficult to keep the hollow fiber membrane filling rate in each of the zones A to H at 13% or more, and it also becomes difficult to form a gap through which the dialyzate flows between the hollow fiber membranes 41, resulted in the deterioration in dialysis performance. Meanwhile, if the wave height is larger than 1.5 mm, the hollow fiber membrane 41 may be collapsed upon the application of crimping to the hollow fiber membrane 41. If the wave length is smaller than 5 mm, the hollow fiber membrane 41 may be collapsed upon the application of crimping to the hollow fiber membrane 41. If the wave length is larger than 30 mm, it becomes difficult to keep the hollow fiber membrane filling rate in each of the zones A to H at 13% or more, and it also becomes difficult to form a gap through which the dialyzate flows between the hollow fiber membranes 41, resulted in the deterioration in dialysis performance. The range can be selected properly depending on the type or shape of the material for the hollow fiber membrane, and is therefore not limited to the above-mentioned range.

The hollow fiber membrane filling rate in the body part of the main body case 10 is preferably 53 to 64%, more preferably 55% to 62%, still more preferably 57 to 60%. If the filling rate is smaller than 53%, the dialyzate may undergo short pass and therefore flows into particular sites, resulted in the deterioration in dialysis performance. If the filling rate is larger than 64%, the hollow fiber membrane 41 may be broken upon the insertion of the hollow fiber membrane bundle 40 into the main body case 10.

When the hollow fiber membrane filling rate in each of the zones A to H is set at 13% or more, the difference between the average value of the hollow fiber membrane filling rates in the zones A to H and the hollow fiber membrane filling rate in the body part is preferably 50% or less, preferably 40% or less, from the viewpoint of the prevention of the disruption of the flow of blood.

With respect to the joint of the headers 21 and 23 to the main body case 10, it is desirable that each of the headers 21 and 23 and the main body case 10 are attached to each other and the headers 21 and 23 are brought into contact with and pressed against the partitioning wall edge faces 31 and 33, respectively, to secure sealing properties, from the viewpoint of the prevention of the accumulation of blood. In this regard, a ring-shaped elastic body made from a silicon rubber or the like may be provided to the header so that the ring-shaped elastic body can be in contact with each of the partitioning wall edge faces 31 and 33 to thereby secure sealing properties. In this case, it is preferred to reduce the size of a space formed by the ring-shaped elastic body as possible, from the viewpoint of the reduction of blood-accumulated parts.

The shape of the ring-shaped elastic body is properly selected in such a manner that the elastic body does not block off the hollow openings of the hollow fiber membranes, with the amount of deformation of the elastic body caused by pressurization, the changes in sizes of the main body case 10 and the headers 21 and 23, the accuracy of assembly of the module and the like taken into consideration. As for the joining method, ultrasonic welding, the joining with a solvent, spin welding, fitting with screws and the like may be employed. Among these, ultrasonic welding is preferred, since high productivity can be achieved and sealing properties can be secured even at joint parts.

The baffle 11 may be a tongue-shaped baffle that does not reach the above-mentioned partitioning walls 30 and 32, multiple tongue-shaped baffles, a ring-shaped baffle, a ring-shaped baffle having slits formed therein, or a baffle of which the tip reaches the partitioning walls 30 and 32.

The materials for the main body case 10 and the headers 21 and 23 are not particularly limited, and polystyrene, polycarbonate, polymethyl methacrylate, polyethylene, polypropylene and the like can be used suitably.

When an embodiment in which a hydrophilic copolymerization polymer having a relaxation time of adsorbed water of $2.5 \times 10^{-8}$ seconds or shorter and $5.0 \times 10^{-10}$ or longer at $-40°$ C. is present on the blood-contacting surface of each of the hollow fiber membranes is combined, the effect of the embodiment of item [3] can become maximum. Therefore, as mentioned in Examples and Comparative Examples below, if the hydrophilic copolymerization polymer is not used, the effect cannot become maximum. That is, when a technique using the hydrophilic copolymerization polymer or the like to improve the blood flow in the center part of the module cross section, it is highly required to care the blood flow in the outermost peripheral part in the cross section and therefore it is considered that the application of this technique can provide a drastic effect.

Further, when particulate protuberances each having a particle diameter 50 nm or more are present on the blood-contacting surface of each of the hollow fiber membranes at a density of more than 3 particles/$\mu m^2$, the effect of the optimization of the distribution of the hollow fiber membranes is not sometimes developed. In this case, it is considered that, although the blood flow is improved, the need of optimizing the blood flow in the outermost peripheral part is increased.

With respect to the headers 21 and 23, if the surface unevenness is high, the activation of blood can be induced, leading to the occurrence of residual blood. Therefore, the roughness (Ra) of the header inner surface is preferably 0.8 $\mu m$ or less, more preferably 0.5 $\mu m$ or less, still more preferably 0.3 $\mu m$ or less. Similarly, the roughness (Ra) of the edge face is preferably 1 $\mu m$ or less, more preferably 0.5 $\mu m$ or less, still more preferably 0.3 $\mu m$ or less.

In addition, the inner diameter of the hollow fiber membrane is preferably 100 to 400 $\mu m$, more preferably 120 to 250 $\mu m$, still more preferably 140 to 200 $\mu m$. The thickness of the membrane is preferably 10 to 100 $\mu m$, more preferably 20 to 70 $\mu m$, still more preferably 30 to 50 $\mu m$.

For the purpose of preventing the occurrence of residual blood in an artificial kidney, the hollow fiber membrane module preferably has the following property: when 2 L of bovine blood having a temperature of 37° C., having a hematocrit value of 30%, the total protein concentration of 6.5 g/dL and a $\beta_2$-microglobulin ($\beta_2$-MG) concentration of 1 mg/L, and containing sodium citrate is allowed to flow through the hollow fiber membrane module at a flow rate of 200 mL/min and a filtration flow rate of 16 mL/min, the ratio of the sieving coefficient of albumin after 5 minutes (Sc-Alb(5)) to that after 20 minutes (Sc-Alb(20)) (i.e., (Sc-Alb (20)/Sc-Alb (5)) is preferably 0.5 to 1.0, more preferably 0.7 to 0.95, and the ratio of the sieving coefficient of $\beta_2$-MG after 5 minutes to that after 20 minutes (i.e., (Sc-$\beta_2$MG (20)/sc-$\beta_2$MG(5)) is 1.01 to 1.20, preferably 1.05 to 1.15. With respect to the overall mass transfer coefficient for urea, the ratio of that in an aqueous system (Ko(W)) to that in a bovine plasma system (Ko(B)) (i.e., (Ko(B)/Ko(W))) is preferably 0.8 or more, more preferably 0.85 or more.

A fact that the Sc-Alb(20)/Sc-Alb(5) value is less than 1 means that a protein or the like is deposited onto the membrane over time and therefore the number or size of pores through which albumin can pass is reduced. In contrast, a fact that the Sc-$\beta_2$MG(20)/Sc-$\beta_2$MG(5) value is larger than 1 means that $\beta_2$-MG is entrapped by the membranes. The difference between these facts is due to the difference in molecular weights of these substances. That is, it is considered that: albumin has a molecular weight of about 6.6000 and the pore sizes of the membrane are so controlled that albumin cannot pass therethrough; on the other hand, $\beta_2$-MG has a molecular weight of about 1.2000, and the pore sizes of the membrane are so controlled that $\beta_2$-MG can path therethrough, and $\beta_2$-MG is trapped in the inside of the membrane.

A fact that the difference in overall mass transfer coefficient for urea is small between an aqueous system and a bovine plasma system means that the stimulation applied to blood cells during blood dialysis therapy may be small, which suggests that the surface configuration of the membrane during the contact of the membrane with water is the same as that during the contact of the membrane with blood. After the dialysis therapy is completed, for returning blood in the separation membrane module into the body, a saline solution is allowed to pass through the membrane module. It is assumed that the alteration in configuration of the surface of the membrane caused by a saline solution may affect the tendency of the occurrence of residual blood. However, it is considered that the use of the hollow fiber membrane according to the present invention rarely causes the alteration in configuration of the surface of the membrane.

The overall mass transfer coefficient for urea can be calculated by measuring a urea clearance. For the measurement of the urea clearance, a hollow fiber membrane module having a surface area of 1.6 m² is preferably used. If it is difficult to produce a 1.6 m² hollow fiber membrane module, a separation membrane module having a surface area close to the above-mentioned value as possible is used for the measurement of the clearance.

The measurement method for urea clearance in an aqueous system is carried out in accordance with dialyzer performance evaluation criteria edited by Japan Society for Artificial Organs (issued on September, 1982). In the criteria, there are mentioned two types of measurement methods. In the present invention, the experiments are carried out employing TMP 0 mmHg as a reference.

The details of the method for measuring urea clearance in bovine plasma are mentioned below. In the case of an artificial kidney, the following conditions are employed: the blood side flow rate is 200 mL/min, the dialyzate side flow rate is 500 mL/min, and the filtration flow rate is 10 mL/min/m². The total protein concentration is 6.5±0.5 g/dL and the urea concentration is 1 g/L.

From the viewpoint of removal performance, the value of the aqueous urea clearance is preferably 180 mL/min or more, more preferably 190 mL/min or more, still more preferably 195 mL/min or more.

The water permeation performance of the hollow fiber membrane module is preferably 200 mL/hr/m²/mmHg or more, more preferably 300 mL/hr/m²/mmHg or more, still more preferably 400 mL/hr/m²/mmHg or more. If the water permeation performance is too high, although internal filtration may occur and the solute removal performance is increased, stimuli on blood cells are also increased. Therefore, the water permeation performance is preferably 2000 mL/hr/m²/mmHg or less, more preferably 1500 mL/hr/m²/mmHg or less, still more preferably 1000 mL/hr/m²/mmHg or less. The water permeation performance (UFR) can be calculated in accordance with the following formula:

$$UFR(\text{mL/hr/m}^2/\text{mmHg}) = Q_w / (P \times T \times A)$$

(wherein $Q_w$: amount of filtration (mL), T: efflux time (hr), P: pressure (mmHg), A: inner surface area of the hollow fiber membrane (m²))

The present invention is described with reference to examples, but the present invention is not limited to these examples.

EXAMPLES (1) Observation of Inner Surface on SEM

A hollow fiber membrane was sliced into a semi-cylindrical shape with a single-edged knife so that the inner surface of the hollow fiber membrane was exposed. Subsequently, a Pt—Pd thin film was formed on the surface of the hollow fiber membrane by sputtering, thereby producing a sample. The inner surface of the hollow fiber membrane sample was observed on a field emission-type scanning electron microscope (S800 manufactured by Hitachi, Ltd.) at a magnification of 50,000 times, and the number of particulate protuberances each having a particle diameter of 50 nm or more in an arbitrary 1 μm² area was counted.

(2) Measurement of Relaxation Time

In the invention of the present application, dielectric relaxation spectra obtained by a TDR (Time Domain Reflectometry) method and an IMA (Impedance Material Analyzer) method were fitted using the formulae shown below to determine a relaxation time.

$$\varepsilon^* = \varepsilon' + i\varepsilon'' = \varepsilon_\infty + \sum_n \frac{\Delta\varepsilon_n}{1 + (i2\pi f \tau_n)^{\beta_n}} + \sum_m \Delta\varepsilon_m \int_0^\infty \left(-\frac{d\Phi_m}{dt}\right) \exp(-i2\pi f t) dt - i\frac{\sigma}{2\pi f \varepsilon_0} \quad \text{[Formula 1]}$$

wherein $$\varphi m = \exp(-(t/\tau m)^{\beta}m) \quad \text{[Formula 2]}$$

wherein
$\in^*$: a complex dielectric constant, $\in'$: a substantial part of a complex dielectric constant (dielectric constant), $\in''$: an imaginary part of a complex dielectric constant (dielectric loss), $\in\infty$: a dielectric constant when the frequency is infinite, $\Delta\in$: a relaxation strength, τ: a relaxation time, β: a parameter representing the width of distribution of relaxation (0<β≤1), f: a frequency, t: a time, σ: an electrical conductivity, and $\in 0$: a dielectric constant of vacuum.

In the IMA method, an RF impedance/material analyzer 4291B (Hewlett-Packard) was used, wherein the frequency was 1 MHz to 500 MHz.

In the TDR method, an oscilloscope HP54120B (Hewlett-Packard) was used, wherein the frequency was 500 MHz to 20 GHz.

The measurement sample used was an aqueous 40 wt % solution (pure water was used). The sample was set in the device, and the measurement was carried out after cooling the sample to −40° C. and then allowing the sample to stand for about 1 hour. Since bulk water was frozen and therefore the dielectric relaxation was not observed, bulk water could be distinguished from adsorbed water. Water adsorbed onto a polymer is expressed as a peak in which f is observed around $10^{-9}$ to $10^{-10}$ when $\in''$ and f are plotted.

(3) X-Ray Photoelectron Spectrometry (XPS) Measurement

The hollow fiber membrane was sliced into a semi-cylindrical shape with a single-edged knife, and the measurement was performed at arbitrary three points in each of the inner surface and the outer surface of the hollow fiber membrane in the manner mentioned below. The measurement sample was rinsed with ultrapure water, then dried at room temperature at 0.5 Torr for 10 hours and then subjected to the measurement. The following analyzer and conditions were used.

Analyzer: ESCA LAB220iXL
Excitation X-ray: monochromatic Al Kα1,2 radiation (1486.6 eV)
X-ray diameter: 0.15 mm
Photoelectron escape angle: 90° (the tilt of the detector relative to the sample surface).

(4) Measurement of Surface Unevenness

A center line average roughness (Ra) was measured using a contact-type surface roughness meter.

(5) Measurement of Hollow Fiber Membrane Filling Rate

A blood inlet header 21 and a blood outlet header 23 were removed from a blood treatment apparatus 1, the blood treatment apparatus 1 was placed with a dialyzate inlet port 12 and a dialyzate outlet port 13 of a main body case 10 facing down, each of partitioning wall edge faces 31 and 33 was irradiated with ultraviolet ray from an ultraviolet ray irradiation device, and an image of each of the partitioning wall edge faces 31 and 33 was taken. As a light source for ultraviolet ray, a mercury xenon lamp having a center wavelength for irradiated ultraviolet ray of 365 nm was used. As a light guide for the ultraviolet ray irradiation device, a quartz-made optical fiber light guide was used. The shape of the light guide for the ultraviolet ray irradiation device was circular, the angle of irradiation with ultraviolet ray was 60 degrees, the output of ultraviolet ray was 150 W, and the position at which the device was to be set was so adapted that the center of an edge face of the blood treatment apparatus aligned with the center of the light guide and was set at a position 20 mm apart from the edge face of the blood treatment apparatus. As an imaging device, a 7450-pixel line sensor camera was used, and a lens having permeability of light having a wavelength of 200 nm to 450 nm of 70% or more and having a focal length of 105 mm was selected so that 1 pixel corresponds to 7 μm on the edge face of the blood treatment apparatus. The camera was placed at the front of the blood treatment apparatus so that the optical center of the lens aligned with the centers of the blood treatment apparatus and the light guide.

In each of images obtained, outlines of the hollow fiber membranes and outlines of other parts were highlighted by means for a bypass filter. Each of the resulting images was subjected to a binary coded processing at a predetermined threshold value, so that the parts of the hollow fiber membranes had lighter brightness values and other parts had darker brightness values. The threshold value employed was determined by multiplying an average brightness value for an imaged 10 mm square area that was concentric with the centers of the partitioning wall edge faces 31 and 33 by 0.7. Subsequently, inner diameter parts (regions each having a darker brightness value and surrounded by and separated from the regions each having a brighter brightness value) were identified by a known particle analysis technique, and a center coordinate for the inner diameter part of each of the hollow fiber membranes, for which the center of the partitioning wall edge face 31 or the partitioning wall edge face 33 was employed as the origin, was determined. Further, as shown in FIG. 4, a zone lying between a position corresponding to the inner diameter of each of the headers and a position 1 mm apart from the aforementioned position toward the inner periphery was divided at 45° intervals into equal 8 parts with the origin as its center to produce zones A to H, subsequently the number of the hollow fiber membranes 41 each having a center coordinate of the inner diameter part thereof in each of the zones A to H was counted, and the filling rate was calculated from the formula shown below. As the outer diameter of each of the hollow fiber membranes, the header inner diameter D0, and the body part inner diameter D1 of the main body case, designed values were employed.

$$\text{Filling rate in each zone } (\%) = \frac{8 \times (\text{outer diameter of hollow fiber membrane})^2 \times \begin{pmatrix} \text{number of hollow fiber membranes} \\ \text{present in each zone} \end{pmatrix}}{\begin{pmatrix} (\text{inner diameter } D0 \text{ of header})^2 - \\ [(\text{inner diameter } D0 \text{ of header}) - 2]^2 \end{pmatrix}} \times 100 \quad \text{[Formula 3]}$$

$$\text{Filling rate in body part } (\%) = \frac{(\text{outer diameter of hollow fiber membrane})^2 \times \begin{pmatrix} \text{total number of hollow fiber} \\ \text{membranes in blood treatment apparatus} \end{pmatrix}}{\begin{pmatrix} \text{inner diameter } D1 \text{ of body} \\ \text{part of main body case} \end{pmatrix}^2} \times 100 \quad \text{[Formula 4]}$$

(6) Crimp Measurement Method

The pitch and amplitude of a crimp applied to each of the hollow fiber membranes 41 were measured in the following manner. First, both end parts of the main body case 10 of the blood treatment apparatus were cut in a direction vertical to the axis direction at positions each of which was located inside of a partitioning wall as observed in an axis direction. One end of the drawn hollow fiber membrane was fixed, and a load of 1 g was applied to the other end, so that the hollow fiber membrane was allowed to swing down in a vertical direction. The number of wave tops was counted sequentially with starting from an arbitral wave top toward the x-direction, wherein x-axis was the downward direction and y-axis was the rightward direction as observed by an observer. The x-direction distance until the count number became 10 was measured, and one tenth of the direction was defined as the pitch. The wave width in an arbitrary wave top and the wave width in a wave bottom that was nearest from the aforementioned peak top as observed in the x-direction (i.e., a position at which the wave width became minimum in one wave length as observed in the y-direction in one wave length) were measured using a microscope, and one-half of the distance between the wave top and the wave bottom was calculated. The measurement was carried out at different 10 positions, and an average of calculated values for the 10 positions was defined as an amplitude.

(7) Test on the Occurrence of Residual Blood

A blood treatment apparatus 1 was washed with a saline solution by allowing 700 mL in total of a saline solution to flow at a flow rate of 200 mL/min from the blood side with the blood inlet header 21 facing down. In this procedure, no bubble removal operation (e.g. the application of vibrations to the blood treatment apparatus 1) was carried out.

Subsequently, a dialyzate was allowed to flow from the dialyzate side at a flow rate of 500 mL/min, and bovine blood was introduced into the blood side at 100 mL/min. In this manner, dialysis was started. The bovine blood used was added with heparin, and was so prepared as to have a hematocrit value of 30% and the total protein amount of 6.5 g/dL. After it was confirmed that the bovine blood appeared at the blood outlet header 23 through the hollow fiber membranes, the flow rate was altered to 200 mL/min and the blood treatment apparatus 1 was reversed up-and-down so that the blood flowed from the top to the bottom. The blood was allowed flow for 5 minutes while keeping this state. The water removal amount was 0. The returned blood was washed with a saline solution by allowing 300 mL in total of the saline solution to flow from the top to the bottom at a flow rate of 100 mL/min. Subsequently, the number of hollow fiber membranes 41 which were remained in the blood treatment apparatus 1 and in which the blood was remained was counted. The bovine blood was not fresh blood, and therefore the function of platelets was decreased. Therefore, for the evaluation of anti-thrombotic properties of a material, it is necessary to evaluate the material with respect to both this test and the evaluation on the deposition of platelets to the material as mentioned in item (11) below.

(8) Measurement of Sieving Coefficient

Bovine blood (heparin-treated blood) that was kept warm at a temperature of 37° C. and had a hematocrit value 30%, and the total protein amount of 6.5 g/dL was used in a blood tank, and the bovine blood was fed to the inside of the hollow fiber using a pump at a flow rate of 200 mL/min. In this test, the pressure on the module outlet side was so controlled that the filtration amount became 10 mL/min per 1 m² (i.e., 16 mL/min for 1.6 m²), and a filtrate and the blood at the outlet were returned to the blood tank. Five minutes and twenty minutes after the initiation of reflux, the blood at an inlet and an outlet on the hollow fiber side and the filtrate were sampled. The blood was centrifuged into serum and then analyzed using a BCG (bromocresol green) method kit (tradename: A/GB Test Wako (Wako Pure Chemical Industries, Ltd.)), the albumin permeability (%) was calculated from the concentration. In the calculation of the concentration of the filtrate, with respect to the calibration curve for albumin, for the purpose of obtaining good sensitivity and producing a calibration curve at low concentrations, serum albumin included in the kit was diluted properly for the production of the calibration curve.

The sieving coefficient was calculated from concentrations of each solution in accordance with the following formula.

$$\text{Sieving coefficient}(Sc) = CF/(CBi/2+CBo/2) \times 100$$

In the formula, CF: the concentration of a solute in an F solution, CBi: the concentration of a solute in a Bi solution, and CBo: the concentration of a solute in a Bo solution.

(9) Measurement of Urea Performance in Aqueous System

An experiment was carried out in accordance with dialyzer performance evaluation criteria edited by Japan Society for Artificial Organs (issued on September, 1982). In the criteria, there are mentioned two types of measurement methods. In the experiment, TMP 0 mmHg was employed as a reference. The clearance ($C_L$) was calculated in accordance with the following formula.

$$C_L(\text{mL/min}) = \{(CBi-Bo)/CBi\} \times Q_B$$

In the formula, CBi: the concentration of urea at an inlet side of the module, CBo: the concentration of urea at an outlet side of the module; and $Q_B$: the flow rate on the blood side (mL/min).

The overall mass transfer coefficient (Ko) can be calculated from the clearance in accordance with the following formula.

$$Ko = \frac{Q_B}{A(1-Q_B/Q_D)} \ln\left(\frac{1-C_L/Q_D}{1-C_L/Q_B}\right) \quad [\text{Formula 5}]$$

In the formula, Ko: an overall mass transfer coefficient (cm/min), A: a surface area (cm²) of a membrane, and $Q_D$: the flow rate of a dialyzate (mL/min).

(10) Measurement of Urea and $\beta_2$-MG Performance in Bovine Plasma System

Bovine blood having disodium ethylenediaminetetraacetate added thereto was so prepared as to have a hematocrit value of 30% and a total protein amount of 6.5 g/dL.

Subsequently, urea and $\beta_2$-MG were added to the bovine blood so that the urea concentration became 1 g/L and the $\beta_2$-MG concentration became 1 mg/L, and the resulting mixture was agitated. The resulting bovine blood was divided into a 2 L aliquot for circulation and a 1.5 L aliquot for clearance measurement.

Figure 6:
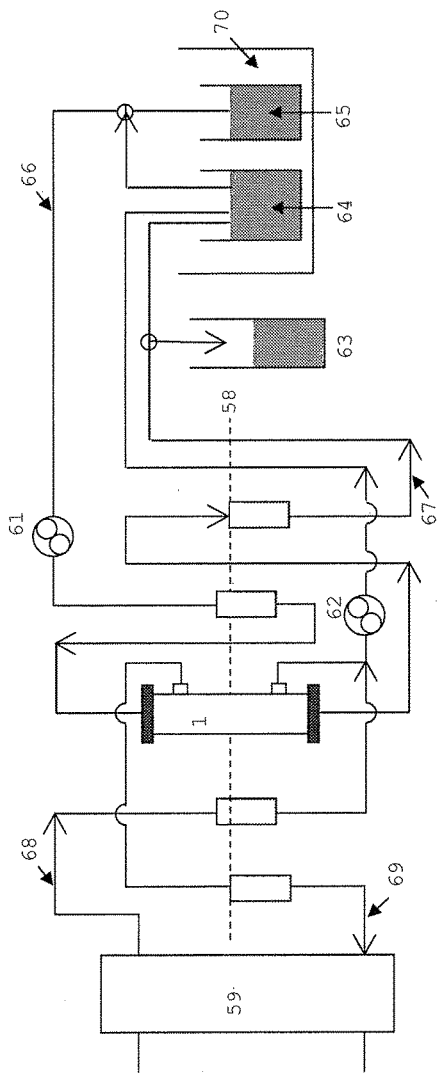
FIG. 6 shows a circuit to be used in a clearance measurement.
Figure 7:
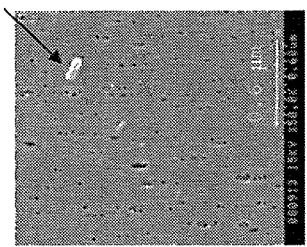
FIG. 7 shows an example of a scanning electron micrograph of a surface in a hollow fiber membrane.

A circuit was assembled as shown in FIG. 6, and a hollow fiber membrane module was set in the circuit. TR2000S manufactured by TORAY MEDICAL CO., LTD. was used as a dialyzer. In FIG. 6, TR2000S corresponds to the Bi pump, the F pump, and the dialyzer.

Dialyzate solutions A and B (Kindaly solution AF No. 2 manufactured by Fuso Pharmaceutical Industries, Ltd.) were placed in the dialyzer. RO water was allowed to flow from the dialyzate side to the blood side. The dialyzate concentration, the temperature, and the dialyzate side flow rate ($Q_D$) were set at 13-15 mS/cm, 34° C. or higher, and 500 mL/minute, respectively.

The water removal rate ($Q_F$) of the dialyzer was set at 10 mL/(min·m²). The inlet of the Bi circuit was placed in a circulation beaker containing 2 L of the bovine blood (37° C.) prepared as mentioned above, and the Bi pump was started. After the liquid from the outlet of the Bo circuit was discarded for 90 seconds, the outlet of the Bo circuit and the outlet of the Do circuit were immediately placed in circulation beakers to form a circulation state. The blood side flow rate ($Q_B$) was set at 200 mL/min.

Subsequently, the F pump of the dialyzer was started to operate. After the circulation was performed for 1 hour, the Bi and F pumps were stopped.

The inlet of the Bi circuit was then placed in the bovine blood prepared as mentioned above for clearance measurement, and the outlet of the Bo circuit was placed in a beaker for discharge. The liquid from the outlet of the Do circuit was discarded.

The Di pump was started. The blood pump was also started, and the space between the trap and the Bi chamber was opened ($Q_B$ 200 mL/min, $Q_D$ 500 mL/min, $Q_F$ 10 mL/(min·m²)).

Two minutes after the start, 10 mL of a sample was collected from the bovine blood (37° C.) for clearance measurement and defined as Bi liquid. Four minutes and 30 seconds after the start, 10 mL of a sample was collected from the outlet of the Bo circuit and defined as Bo liquid. These samples were stored in a freezer at −20° C. or lower.

A clearance was calculated from the concentration of each solution in the same manner as mentioned above. With respect to urea, the overall mass transfer coefficient was determined.

(11) Method for Testing Deposition of Human Platelets on Hollow Fiber Membrane

A double-side tape was bonded to an 18 mmφ polystyrene circular plate, and the hollow fiber membrane was fixed thereon. The bonded hollow fiber membrane was sliced into a semi-cylindrical shape with a single-edged knife so that the inner surface of the hollow fiber membrane was exposed. It should be carefully performed, because if there is dirt, a scratch, a fold, or the like on the inner surface of the hollow fiber, platelets may be deposited on such a portion so that the evaluation may not be correctly performed. The circular plate was bonded to a cylindrical cut piece of Falcon (registered trademark) tube (No. 2051, 18 mmφ) so that the hollow fiber membrane-carrying surface was placed inside the cylinder, and the gap was filled with Parafilm. The interior of the cylindrical tube was washed with a saline solution and then filled with a saline solution. Heparin was added at a concentration of 50 U/mL to human venous blood immediately after the blood sampling. After the saline solution was discharged from the cylindrical tube, 1.0 mL of the blood was placed in the cylindrical tube within 10 minutes after the sampling and shaken at 37° C. for 1 hour. Thereafter, the hollow fiber membrane was washed with 10 mL of a saline solution, and the blood component was fixed thereon with a 2.5% by volume glutaraldehyde saline solution and washed with 20 mL of distilled water. The washed hollow fiber membrane was dried at room temperature under a reduced pressure of 0.5 Torr for 10 hours. The hollow fiber membrane was then bonded to the sample stage of a scanning electron microscope with a double-side tape. A Pt—Pd thin film was then formed on the surface of the hollow fiber membrane by sputtering, thereby producing a sample. The inner surface of the hollow fiber membrane was observed on a field emission-type scanning electron microscope (S800 manufactured by Hitachi, Ltd.) at a magnification of 1,500 times, and the number of the deposited platelets per field ($4.3 \times 10^3$ μm²) was counted. The number of the deposited platelets (/$4.3 \times 10^3$ μm²) was defined as the average of the numbers of the deposited platelets which were counted in ten different fields at and around the longitudinal center of the hollow fiber. When the number of the deposited platelets per field exceeded 100 (/$4.3 \times 10^3$), the result was counted as 100. The longitudinal ends of the hollow fiber were omitted from the objects to be measured for the number of deposits, because blood tended to stay thereon. The number of the deposited platelets is preferably 20(/($4.3 \times 10^3$ μm²)) or less.

(12) Measurement of Flexible Layer on the Inner Surface of Hollow Fiber Membrane The hollow fiber membrane was sliced into a semi-cylindrical shape with a single-edged knife, and the inner surface was measured on an atomic force microscope (AFM). The measurement sample was rinsed with ultrapure water, then dried at room temperature at 0.5 Torr for 10 hours, and then used for the measurement.

The hollow fiber membrane was attached onto a sample stage, water droplets were dropped over the membrane to moisten the membrane, thereby making the membrane in a moistened state having a water content of 65% by weight or more. In this state, a force curve measurement was carried out in a contact mode. A careful attention was paid so as not to dry the surface of the sample during the measurement. When a flexible layer is present on the surface in the approach of a cantilever to the sample, a curved part can be observed. The distance of the curved part was defined as a flexible layer. The measurement was carried out at 20 parts, and an average value of the results was used. With respect to the average value employed, the first decimal place of the average value was rounded off.

The AFM observation conditions were as follows: a scanning probe microscope SPM 9500-J3 (SHIMADZU, Kyoto, Japan) was used as an apparatus, the observation mode was a contact mode, the probe used was NP-S (120 mm, wide) (Nihon VEECO KK, Tokyo, Japan), the scanning range was 5 μm×5 μm, and the scanning speed was 1 Hz.

(Production of Hollow Fiber Membrane 1-1)

Sixteen parts by weight of polysulfone (Udel-P3500, Amoco), 2 parts by weight of PVP (K90, ISP) and 4 parts by weight of PVP (K30, ISP) were dissolved by heating at 90° C. for 10 hours together with 77 parts by weight of DMAc and 1 part by weight of water while agitating with an impeller at 50 rpm, thereby preparing a membrane forming stock solution. The stock solution was stored at 60° C. for 48 hours and then spun.

The membrane forming stock solution was fed to a spinning nozzle at a temperature of 50° C. and then ejected through a double annular slit tube having a circular slit section with an outer diameter of 0.35 mm and an inner diameter of 0.25 mm, and a solution comprising 65 parts by weight of DMAc and 35 parts by weight of water was ejected through an intercircular section as a core injection solution (hereinbelow, also referred to as "injection solution" for convenience). After the formation of a hollow fiber membrane, the hollow fiber membrane was allowed to pass through a 350 mm dry-zone atmosphere at a temperature of 30° C. and a relative humidity of 75% RH and then through a coagulation bath of 14% by weight of DMAc and 86% by weight of water at a temperature of 40° C. The hollow fiber membrane was then subjected to a water washing process at 85° C. for 120 seconds, a drying process at 130° C. for 2 minutes, and a crimping process. The resulting hollow fiber membrane 1-1 was wound into a bundle. The hollow fiber membrane immediately before the drying step had a tensile force of 67 g/mm². The hollow fiber membrane had an inner diameter of 195 μm and a thickness of 40 μm. The shape of a crimp was determined, and it was found that the crimp had a wave height of 0.3 mm (amplitude: 0.15 mm) and a wave length (pitch) of 8.0 mm.

(Production of Hollow Fiber Membrane 1-2)

Spinning was carried out under the same conditions as employed for the production of the hollow fiber membrane 1-1. The resulting hollow fiber membrane had an inner diameter of 200 μm and a thickness of 40 μm. The shape of a crimp was determined, and it was found that the crimp had a wave height of 0.2 mm (amplitude: 0.1 mm) and a wave length (pitch) of 8.0 mm.

(Production of Hollow Fiber Membrane 2-1)

Sixteen parts by weight of polysulfone (Udel-P3500, Amoco), 2 parts by weight of PVP (K90, ISP) and 4 parts by weight of PVP (K30, ISP) were dissolved by heating at 80°

C. for 10 hours together with 77 parts by weight of DMAc and 1 part by weight of water while agitating with an impeller at 50 rpm, thereby preparing a membrane forming stock solution. The stock solution was stored at 60° C. for 48 hours and then spun.

The membrane forming stock solution was fed to a spinning nozzle at a temperature of 50° C. and then ejected through a double annular slit tube having a circular slit section with an outer diameter of 0.35 mm and an inner diameter of 0.25 mm, and a solution prepared by dissolving 10 parts by weight of a vinylpyrrolidone-vinyl acetate copolymerization polymer (60/40 (by weight)) in a solution comprising 63 parts by weight of DMAc and 37 parts by weight of water was ejected through an intercircular section as a core injection solution. After the formation of a hollow fiber membrane, the hollow fiber membrane was allowed to pass through a 350 mm dry-zone atmosphere at a temperature of 28° C. and a relative humidity of 95% RH and then through a coagulation bath of 14% by weight of DMAc and 86% by weight of water at a temperature of 40° C. The hollow fiber membrane was then subjected to a water washing process at 80° C. for 120 seconds, a drying process at 130° C. for 2 minutes, and a crimping process. The resulting hollow fiber membrane (2) was wound into a bundle. The hollow fiber membrane immediately before the drying step had a tensile force of 113 g/mm². The hollow fiber membrane had an inner diameter of 185 μm and a thickness of 38 μm. The shape of a crimp was determined, and it was found that the crimp had a wave height of 0.4 mm (amplitude: 0.2 mm) and a wave length (pitch) of 8.0 mm.

(Production of Hollow Fiber Membrane 2-2)

Spinning was carried out under the same conditions employed for the production of the hollow fiber membrane 2-1. The resulting hollow fiber membrane had an inner diameter of 200 μm and a thickness of 40 μm. The shape of a crimp was determined, and it was found that the crimp had a wave height of 0.2 mm (amplitude: 0.1 mm) and a wave length (pitch) of 8.0 mm.

(Production of Hollow Fiber Membrane 2-3)

Spinning was carried out under the same conditions employed for the production of the hollow fiber membrane 2-1. The resulting hollow fiber membrane had an inner diameter of 200 μm and a thickness of 40 μm. The shape of a crimp was determined, and it was found that the crimp had a wave height of 1.7 mm (amplitude: 0.85 mm) and a wave length (pitch) of 17 mm.

(Production of Hollow Fiber Membrane 3)

Eighteen % by weight of polysulfone (Udel-P3500, Amoco) and 9% by weight of a vinylpyrrolidone-vinyl acetate copolymerization polymer (60/40 (by weight)) were dissolved by heating at 90° C. for 10 hours together with 72% by weight of DMAc and 1% by weight of water while agitating with an impeller at 50 rpm, thereby preparing a membrane forming stock solution. The stock solution was stored at 60° C. for 48 hours and then spun.

The membrane forming stock solution was fed to a spinning nozzle at a temperature of 45° C. and then ejected through a double annular slit tube having a circular slit section with an outer diameter of 0.35 mm and an inner diameter of 0.25 mm, and a solution comprising 60% by weight of DMAc and 40% by weight of water was ejected through an intercircular section as a core injection solution. After the formation of a hollow fiber membrane, the hollow fiber membrane was allowed to pass through a 350 mm dry-zone atmosphere at a temperature of 30° C. and a relative humidity of 70% RH and then through a coagulation bath of 14% by weight of DMAc and 86% by weight of water at a temperature of 40° C. The hollow fiber membrane was then subjected to a water washing process at 80° C. for 120 seconds, a drying process at 130° C. for 2 minutes, and a crimping process. The resulting hollow fiber membrane (3) was wound into a bundle. The hollow fiber membrane immediately before the drying step had a tensile force of 33 g/mm². The hollow fiber membrane had an inner diameter of 200 μm and a thickness of 40 μm. The shape of a crimp was determined, and it was found that the crimp had a wave height of 0.3 mm (amplitude: 0.15 mm) and a wave length (pitch) of 7.0 mm.

(Production of Hollow Fiber Membrane 4)

Seventeen parts by weight of polysulfone (Udel-P3500, Amoco) and 5 parts by weight of PVP (K90, ISP) were dissolved by heating at 50° C. for 48 hours together with 77 parts by weight of DMAc and 1 part by weight of water while agitating with an impeller at 10 rpm, thereby preparing a membrane forming stock solution. The stock solution was stored at 55° C. for 48 hours and then spun.

The membrane forming stock solution was fed to a spinning nozzle at a temperature of 70° C. and then ejected through a double annular slit tube having a circular slit section with an outer diameter of 0.35 mm and an inner diameter of 0.25 mm, and a solution comprising 57 parts by weight of DMAc and 43 parts by weight of water was ejected as a core injection solution. After the formation of a hollow fiber membrane, the hollow fiber membrane was allowed to pass through a 350 mm dry-zone atmosphere at a temperature of 55° C. and a relative humidity of 75% RH and then through a coagulation bath of 14% by weight of DMAc and 86% by weight of water at a temperature of 65° C. The hollow fiber membrane was then subjected to a water washing process at 85° C. for 120 seconds to bundle together, a drying process at 80° C. for 7 hours, and a crimping process. The resulting hollow fiber membrane (4) was wound into a bundle. The hollow fiber membrane had an inner diameter of 190 μm and a thickness of 45 μm. The shape of a crimp was determined, and it was found that the crimp had a wave height of 0.3 mm (amplitude: 0.15 mm) and a wave length (pitch) of 8.0 mm.

(Production of Hollow Fiber Membrane 5)

Eighteen % by weight of polysulfone (Udel-P3500, Amoco) was dissolved by heating at 90° C. for 10 hours together with 81% by weight of DMAc and 1% by weight of water while agitating with an impeller at 50 rpm, thereby preparing a membrane forming stock solution. The stock solution was stored at 60° C. for 48 hours and then spun.

The membrane forming stock solution was fed to a spinning nozzle at a temperature of 50° C. and then ejected through a double annular slit tube having a circular slit section with an outer diameter of 0.35 mm and an inner diameter of 0.25 mm, and a solution comprising 63% by weight of DMAc and 37% by weight of water was ejected through an intercircular section as a core injection solution. After the formation of a hollow fiber membrane, the hollow fiber membrane was allowed to pass through a 350 mm dry-zone atmosphere at a temperature of 30° C. and a relative humidity of 70% RH and then through a coagulation bath of 20% by weight of DMAc and 80% by weight of water at a temperature of 40° C. The hollow fiber membrane was then subjected to a water washing process at 60° C. for 90 seconds, and a crimping process. The resulting hollow fiber membrane (5) was wound into a bundle. The hollow fiber membrane had an inner diameter of 200 μm and a thickness of 40 μm. The shape of a crimp was determined, and it was found that the crimp had a wave height of 0.3 mm (amplitude: 0.15 mm) and a wave length (pitch) of 8.0 mm.

Example 1

Nine thousand and seven hundred hollow fiber membranes 1-1 were inserted into a case having an inner diameter of 36 mm, and the edge face part of the case was blown to disperse the hollow fiber membranes therein. Both ends of the hollow fiber membranes were respectively fixed to the edge parts of the case with a potting material, and a portion of the end of the potting material was cut to open the hollow fiber membranes at the both ends. The effective length of each of the hollow fiber membranes was 26.4 cm. A header part was attached to the resulting product, thereby producing a hollow fiber membrane module (a). The hollow fiber membrane filling rate in a zone lying between the outermost periphery and a position located 1 mm apart from the outermost periphery toward the inner periphery in the edge face part was 47%, the hollow fiber membrane filling rate in a center part was 62%, wherein the difference between the filling rates was 15%. The Ra of the edge face part was 0.2 µm, and the Ra of the inner surface of the header was 0.5 µm.

As the hydrophilic copolymerization polymer, a vinylpyrrolidone-vinyl acetate copolymerization polymer (70/30 (by weight)) was used. The relaxation time of the polymer at −40° C. was $2.2 \times 10^{-8}$ seconds. A mixed aqueous solution of 0.01% by weight of the polymer and 0.1% by weight of n-propanol was prepared, and the mixed aqueous solution was allowed to pass from the blood side inlet Bi (22) toward the blood side outlet Bo (24) of the hollow fiber membrane module at 500 mL/min for 1 minute. Subsequently, the mixed aqueous solution was allowed to pass from the blood side inlet Bi (22) toward the dialyzate side inlet Di (12) at 500 mL/min for 1 minute. In the aqueous solution used, dissolved oxygen was removed therefrom. The filling solution was pushed out from the dialyzate side toward the blood side with 100 kPa of compressed air, so that the mixed aqueous solution did not remain in the module case besides the hollow fiber membranes being in a moistened state. The water content in the hollow fiber membranes was 2.8 times the dried weight of the hollow fiber membranes.

Thereafter, the module was blown with nitrogen at a flow rate of 10 mL/min at each of the dialyzate side and the blood side for 1 minute to purge the inside of the module with nitrogen, the module was then plugged, and the module was irradiated with 25 kGy of γ-ray within 1 week. The oxygen concentration in the module was 1%. The module was subjected to various tests. In ESCA, since a vinylpyrrolidone-vinyl acetate copolymerization polymer was used as the hydrophilic copolymerization polymer, the amount of carbon derived from an ester group can be observed. The ester (COO) carbon peak was observed at an energy +4.0 to +4.2 eV higher than the main C1s peak derived from CH or C—C (at about 285 eV). Therefore, after peak deconvolution was performed, the ratio of the corresponding peak area to the peak area of all elements (all elements except for the hydrogen atom, which was not detectable) was calculated so that the ester carbon content (atm %) was determined. Thus, there are two types of nitrogen atoms, i.e., a nitrogen atom derived from PVP and a nitrogen atom derived from the vinylpyrrolidone-vinyl acetate copolymerization polymer, and the ratio of these two types of nitrogen atoms can be calculated on the basis of the amount of carbon derived from an ester group. Further, all of sulfur atoms are derived from polysulfone. From these results, the amount of the vinylpyrrolidone-vinyl acetate copolymerization polymer on the surface can be calculated. In the case of a vinylpyrrolidone-vinylcaprolactam copolymerization polymer or an ethylene glycol-propylene glycol copolymerization polymer, the amount can also be calculated from the amounts of carbon atoms, oxygen atoms, nitrogen atoms and sulfur atoms.

Example 2

A hollow fiber membrane module (a) that was produced in the same manner as in Example 1 was used, and a vinylpyrrolidone-vinyl acetate copolymerization polymer (60/40 (by weight)) was used as the hydrophilic copolymerization polymer. The relaxation time of the polymer was $1.6 \times 10^{-8}$ seconds at −40° C. An aqueous solution containing 0.01% by weight of the polymer was prepared, and the hollow fiber membranes were moistened in the same manner as in Example 1, were then purged with nitrogen, and were then irradiated with 25 kGy of γ-ray within 1 week. The water content in the hollow fiber membranes was 2.7 times the dried weight of the hollow fiber membranes. The module was subjected to various tests.

Example 3

The hollow fiber membrane module (a) was used, and a vinylpyrrolidone-vinyl acetate copolymerization polymer (50/50 (by weight)) was used as the hydrophilic copolymerization polymer. The relaxation time of the polymer was $1.4 \times 10^{-8}$ seconds at −40° C. A mixed aqueous solution containing 0.01% by weight of the polymer and 0.1% by weight of ethanol was prepared, and the hollow fiber membranes were moistened in the same manner as in Example 1, were then purged with nitrogen, and were then irradiated with 25 kGy of γ-ray within 1 week. The water content in the hollow fiber membranes was 2.8 times the dried weight of the hollow fiber membranes. The module was subjected to various tests.

Example 4

Ten thousand hollow fiber membranes 1-2 were inserted into a case having an inner diameter of 36 mm, and the edge face part of the case was blown to disperse the hollow fiber membranes therein. Both ends of the hollow fiber membranes were respectively fixed to the edge parts of the case with a potting material, and a portion of the end of the potting material was cut to open the hollow fiber membranes at the both ends. The effective length of each of the hollow fiber membranes was 26.8 cm. A header part was attached to the resulting product, thereby producing a hollow fiber membrane module (b). The hollow fiber membrane filling rate in a zone lying between the outermost periphery and a position located 1 mm apart from the outermost periphery toward the inner periphery in the edge face part was 30%, the hollow fiber membrane filling rate in a center part was 58%, wherein the difference between the filling rates was 28%. The overall filling rate was 53%. The Ra of the edge face part was 0.2 µm, and the Ra of the inner surface of the header was 0.5 µm.

Subsequently, the inside of the module was purged with nitrogen in the same manner as in Example 1 without moistening the hollow fiber membranes, and the module was irradiated with 25 kGy of electron beam within 1 week. The oxygen concentration in the module was 1%. The module was subjected to various tests.

Example 5

Nine thousand and six hundred hollow fiber membranes 3 were inserted into a case having an inner diameter of 36 mm, and the edge face part of the case was blown to disperse the hollow fiber membranes therein. Both ends of the hollow fiber membranes were respectively fixed to the edge parts of the case with a potting material, and a portion of the end of the potting material was cut to open the hollow fiber membranes at the both ends. The effective length of each of the hollow fiber membranes was 26.3 cm. A header part was attached to the resulting product, thereby producing a hollow fiber membrane module (c). The hollow fiber membrane filling rate in a zone lying between the outermost periphery and a position located 1 mm apart from the outermost periphery toward the inner periphery in the edge face part was 48%, the hollow fiber membrane filling rate in a center part was 63%, wherein the difference between the filling rates was 15%. The overall filling rate was 58%. The Ra of the edge face part was 0.2 µm, and the Ra of the inner surface of the header was 0.5 µm.

Subsequently, the inside of the module was purged with nitrogen in the same manner as in Example 1 without moistening the hollow fiber membranes, and the module was irradiated with 25 kGy of γ-ray within 1 week. The oxygen concentration in the module was 1%. The module was subjected to various tests.

Example 6

The hollow fiber membranes 2-2 were used, and about 9600 the hollow fiber membranes were bound up to produce a hollow fiber membrane bundle 40. The hollow fiber membrane bundle was inserted into a polypropylene case (a main body case 10) having a full length of 282 mm, a body inner diameter D1 of 35.1 mm, an edge part inner diameter of 39.3 mm and a body length of 237 mm in such a manner that both ends of the bundle protruded outside of the main body case 10. The hollow fiber membrane filling rate in the body part of the main body case was 61.1%. Subsequently, parts around the outer peripheries of the both ends of the hollow fiber membrane bundle 40 protruded from the main body case 10 were air-blown at a flow rate of 1.5 L/min using a Taslan nozzle to diffuse the hollow fiber membrane bundle. Each of the both ends of the hollow fiber membrane bundle was bundled together using a cover plate that was formed by bonding two plates each having a semicircular cutout section together and had a diameter of 38 mm, a carbon dioxide laser having an output level of 80 W was defocused to an edge face to irradiate the edge face with the laser at a predetermined pattern, thereby sealing the hollow part of the hollow fiber membrane 41. Subsequently, a cap having a length that was enough to get stuck in the center part of the edge face of the hollow fiber membrane bundle and did not reach each of subsequently-formed partitioning walls 31 and 33 of the edge faces and equipped with a tip-sharp protrusion was attached to each of both ends of the main body case 10, a urethane resin was injected through a dialyzate inlet port 12 and a dialyzate outlet port 13 and then cured under centrifugation to thereby form the partitioning walls 30 and 32, thereby fixing the hollow fiber membrane bundle 40 to the inner walls of both edge parts of the main body case 10. Each of the partitioning walls 30 and 32 thus formed was cut with a sharp cutter at a position 1.5 mm apart from each of the ends of the main body case 10, thereby forming an edge face of each of the partitioning walls 31 and 33 and opening the hollow fiber membrane 41. Images of the edge faces of the partitioning walls 31 and 33 were taken using a camera, and the hollow fiber membrane filling rate in each of the zones A to H was calculated. Subsequently, headers 21 and 23 each having an edge inner diameter D0 of 37.3 mm were welded to the main body case 10 by applying ultrasonic wave, plugs were attached thereto, and the resulting product was packaged and then sterilized by the irradiated with 25 kGy of γ-ray, thereby completing a hollow fiber membrane module (d-1). The hollow fiber membrane module was used to carry out various tests.

Example 7

The same procedure as in Example 6 was carried out, except using hollow fiber membranes 2-3, thereby producing a hollow fiber membrane module (d-2). The hollow fiber membrane module was used to carry out various tests.

Example 8

The same procedure as in Example 6 was carried out, except that a cover plate produced using two plates each having a semicircular cutoff part and having a diameter of 33.8 mm for the sealing of the hollow part was used and headers 21 and 23 each having a header inner diameter D0 of 35.1 mm was used, thereby producing a hollow fiber membrane module (e). The hollow fiber membrane module was used to carry out various tests.

Example 9

The same procedure as in Example 6 was carried out, except using hollow fiber membranes 1-2, thereby producing a hollow fiber membrane module (d-3). However, in this example, prior to the irradiation with γ-ray, a vinylpyrrolidone-vinylcaprolactam copolymerization polymer (50/50 (by weight)) was used as the hydrophilic copolymerization polymer, a mixed aqueous solution of 0.01% by weight of the polymer and 0.1% by weight of ethanol was prepared, and the mixed aqueous solution was allowed to pass from the blood side inlet Bi (22) toward the blood side outlet Bo (24) of the hollow fiber membrane module at 500 mL/min for 1 minute. Subsequently, the mixed aqueous solution was allowed to pass from the blood side inlet Bi (22) toward the dialyzate side inlet Di (12) at 500 mL/min for 1 minute. In the aqueous solution used, dissolved oxygen was removed therefrom. The filling solution was pushed out from the dialyzate side toward the blood side with 100-kPa compressed air and then the solution located on the blood side was blown while keeping the dialyzate side in a pressurized state, so that the mixed aqueous solution did not remain in the module case besides the hollow fiber membranes being in a moistened state. The water content in the hollow fiber membranes was 2.8 times the dried weight of the hollow fiber membranes.

Thereafter, the module was blown with nitrogen at a flow rate of 10 mL/min at each of the dialyzate side and the blood side for 1 minute to purge the inside of the module with nitrogen, the module was then plugged, and the module was irradiated with 25 kGy of γ-ray within 1 week. The oxygen concentration in the module was 1%. The module was subjected to various tests.

Example 10

A γ-ray-irradiated hollow fiber membrane module was produced in the same manner as in Example 9, except that hollow fiber membranes 1-2 were used and an ethylene glycol-propylene glycol copolymerization polymer (20/80 (by weight)) was used as the hydrophilic copolymerization polymer. The relaxation time of the polymer was $1.5 \times 10^{-8}$ seconds at −40° C. A mixed aqueous solution containing 0.01% by weight of the polymer and 0.1% by weight of ethanol was prepared, and the hollow fiber membranes were moistened in the same manner as in Example 1, were then purged with nitrogen, and were then irradiated with 25 kGy of γ-ray within 1 week. The water content in the hollow fiber membranes was 2.8 times the dried weight of the hollow fiber membranes. The module was subjected to various tests.

Example 11

A hollow fiber membrane module was produced in the same manner as in Example 1, except that a vinylpyrrolidone-vinylcaprolactam copolymerization polymer (50/50 (by weight)) was used as the hydrophilic copolymerization polymer and a mixed aqueous solution containing 1% by weight of the polymer and 0.1% by weight of n-propanol was prepared and the same procedures were carried out. However, in this example, the filling solution was pushed out from the dialyzate side toward the blood side with 0.2 MPa of compressed air and then the solution located on the blood side was blown at a maximum pressure of 0.2 MPa, a minimum pressure of 0.1 MPa, a flow rate of 20 L (Normal)/min and an air application frequency of 1 time/sec (blowing air five times at the maximum pressure/minimum pressure for 5 seconds; i.e., blowing air at the maximum pressure for 0.5 seconds and blowing air at the minimum pressure for 0.5 seconds), while keeping the pressure in the dialyzate side at 0.2 MPa, thereby removing an excess portion of the copolymerization polymer and rendering only the hollow fiber membranes in a moistened state. The water content in the hollow fiber membranes was 2.8 times the dried weight of the hollow fiber membranes.

Thereafter, the module was blown with nitrogen at a flow rate of 10 mL/min at each of the dialyzate side and the blood side for 1 minute to purge the inside of the module with nitrogen, the module was then plugged, and the module was irradiated with 25 kGy of γ-ray within 1 week. The oxygen concentration in the module was 1%. The module was subjected to various tests.

Comparative Example 1

A hollow fiber membrane module (a) produced in the same manner as in Example 1 was used, but only a matter that PVP (ISP) K90 was used in place of the hydrophilic copolymerization polymer was different. The relaxation time of the PVP was $2.6 \times 10^{-8}$ seconds at −40° C. An aqueous solution containing 0.01% by weight of the PVP was prepared, and the hollow fiber membranes were moistened in the same manner as in Example 1, were then purged with nitrogen, and were then irradiated with 25 kGy of electron beam within 1 week. The water content in the hollow fiber membranes was 2.7 times the dried weight of the hollow fiber membranes. The module was subjected to various tests.

Comparative Example 2

Ten thousand hollow fiber membranes 4 were inserted into a case having an inner diameter of 40 mm, and the edge face part of the case was blown to disperse the hollow fiber membranes therein. Both ends of the hollow fiber membranes were respectively fixed to the edge parts of the case with a potting material, and a portion of the edge part of the potting material was cut to open the hollow fiber membranes at the both ends. The effective length of each of the hollow fiber membranes was 26.4 cm. A header part was attached to the resulting product, thereby producing a hollow fiber membrane module (g). The hollow fiber membrane filling rate in a position located 1 mm apart from the outermost periphery toward the inner periphery in the edge face was 22%, the hollow fiber membrane filling rate in a center part was 52%, wherein the difference between the filling rates was 30%. The overall filling rate was 49%. The Ra of the edge face part was 0.9 μm, and the Ra of the inner surface of the header was 0.5 μm.

As the hydrophilic copolymerization polymer, a vinylpyrrolidone-vinyl acetate copolymerization polymer (70/30 (by weight)) was used. An aqueous solution containing 0.01% by weight of the polymer was prepared, and the hollow fiber membranes were moistened in the same manner as in Example 1, were then purged with nitrogen, and were then irradiated with 25 kGy of γ-ray within 1 week. The water content in the hollow fiber membranes was 2.7 times the dried weight of the hollow fiber membranes. The module was subjected to various tests.

Comparative Example 3

The same procedure as in Example 6 was carried out, except that a cover plate produced using two plates each having a semicircular cutoff part and having a diameter of 36 mm for the sealing of the hollow part was used, thereby producing a hollow fiber membrane module (d-4). The hollow fiber membrane module was used to carry out various tests.

Comparative Example 4

The same procedure as in Example 6 was carried out, except that air blowing was not carried out, thereby producing a hollow fiber membrane module (d-5). The hollow fiber membrane module was used to carry out various tests.

Comparative Example 5

The same procedure as in Example 6 was carried out, except that a cover plate produced using two plates each having a semicircular cutoff part and having a diameter of 45 mm for the sealing of the hollow part was used, headers 21 and 23 each having a header inner diameter D0 of 44.3 mm were used, and a main body case 10 having an edge part inner diameter of 46.3 mm was used, thereby producing a hollow fiber membrane module (h). The hollow fiber membrane module was used to carry out various tests.

Comparative Example 6

A γ-ray-irradiated hollow fiber membrane module was produced in the same manner as in Example 9, except that hollow fiber membranes 1-2 were used and PVP (ISP) K90 was used in place of the hydrophilic copolymerization polymer. The hollow fiber membranes were moistened in the same manner as in Example 1, were then purged with nitrogen, and were then irradiated with 25 kGy of γ-ray within 1 week. The water content in the hollow fiber membranes was 2.8 times the dried weight of the hollow fiber membranes. The module was subjected to various tests.

Comparative Example 7

The same procedure as in Example 1 was carried out, except that a vinylpyrrolidone-vinylcaprolactam copolymerization polymer (50/50 (by weight)) was used as the hydrophilic copolymerization polymer and the concentration of the polymer employed was 1% by weight. Since the discharge of the aqueous solution was also carried out in the same manner as in Example 1, the conditions employed in this comparative example were those which could cause unevenness readily. Within 1 week after the purging with nitrogen, the module was irradiated with 25 kGy of γ-ray. The water content in the hollow fiber membranes was 2.8 times the dried weight of the hollow fiber membranes. The module was subjected to various tests.

TABLE 1

| | | Polymer composition of stock solution[2] [wt %] | Composition of injection solution [wt %] | inner diameter/thickness [μm] | wave height/wavelength [mm] | MD[3] No | Introduction of hydrophilic copolymerization polymer[4] | Relaxation time of adsorbed water [sec] | Amount of copolymerization polymer [wt %] Inner surface | Amount of copolymerization polymer [wt %] Outer surface | Inner surface flexible layer [nm] | Particulate protuberances [particles/μm²] | Number of platelets adhered [particles/(4.3 × 10³ μm²)] | Residual blood test [fiber membranes] |
|---|---|---|---|---|---|---|---|---|---|---|---|---|---|---|
| Example 1 | 1-1 | PSf/PVP(K30)/PVP(K90) 16/4/2 | DMAc/water 65/35 | 195/40 | 0.3/8.0 | a | Membranes were irradiated with γ-ray in mixed aqueous VP/VAc(70/30) + Pro solution | $2.2 \times 10^{-8}$ | 13 | N.D. | 10 | 0.3 | 18 | 6 |
| Example 2 | 1-1 | PSf/PVP(E30)/PVP(K90) 16/4/2 | DMAc/water 65/35 | 195/40 | 0.3/8.0 | a | Membranes were irradiated with γ-ray in aqueous VP/VAc(60/40) solution | $1.6 \times 10^{-8}$ | 18 | N.D. | 15 | 0.3 | 0.2 | 0 |
| Example 3 | 1-1 | PSf/PVP(K30)/PVP(K90) 16/4/2 | DMAc/water 65/35 | 195/40 | 0.3/8.0 | a | Membranes were irradiated with γ-ray in mixed aqueous VP/VAc(50/50) + Et solution | $1.4 \times 10^{-8}$ | 33 | N.D. | 16 | 0.3 | 0.2 | 0 |
| Example 4 | 2-1 | PSf/PVP(K30)/PVP(K90) 16/4/2 | DMAc/water/VA64 63/37/10 | 185/38 | 0.4/8.0 | b | VP/VAc(60/40) was added to injection solution | $1.6 \times 10^{-8}$ | 15 | N.D. | 14 | 0.2 | 0.5 | 1 |
| Example 5 | 3 | PSf/VA64 18/9 | DMAc/water 60/40 | 200/40 | 0.3/7.0 | c | VP/VAc(60/40) was added to spinning solution | $1.6 \times 10^{-8}$ | 19 | 9 | 15 | 0.1 | 1 | 0 |
| Example 6 | 2-2 | PSf/PVP(K30)/PVP(K90) 16/4/2 | DMAc/water/VA64 63/37/10 | 200/40 | 0.2/8.0 | d-1 | VP/VAc(60/40) was added to injection solution | $1.6 \times 10^{-8}$ | 15 | N.D. | 14 | 0.2 | 0.5 | 0 |
| Example 7 | 2-3 | PSf/PVP(K30)/PVP(K90) 16/4/2 | DMAc/water/VA64 63/37/10 | 200/40 | 1.7/17 | d-2 | VP/VAc(60/40) was added to injection solution | $1.6 \times 10^{-8}$ | 15 | N.D. | 14 | 0.2 | 0.5 | 1 |
| Example 8 | 2-2 | PSf/PVP(K30)/PVP(K90) 16/4/2 | DMAc/water/VA64 63/37/10 | 200/40 | 0.2/8.0 | e | VP/VAc(60/40) was added to injection solution | $1.6 \times 10^{-8}$ | 15 | N.D. | 14 | 0.2 | 0.5 | 1 |
| Example 9 | 1-2 | PSf/PVP(K30)/PVP(K90) 16/4/2 | DMAc/water 65/35 | 200/40 | 0.2/8.0 | d-3 | Membranes were irradiated with γ-ray in mixed aqueous VP/VC(50/50) + Et solution | $1.0 \times 10^{-8}$ | 22 | N.D. | 15 | 0.3 | 1 | 1 |
| Example 10 | 1-2 | PSf/PVP(K30)/PVP(K90) 16/4/2 | DMAc/water 65/35 | 200/40 | 0.2/8.0 | d-3 | Membranes were irradiated with γ-ray in mixed aqueous EG/PG(20/80) + Et solution | $1.5 \times 10^{-8}$ | 18 | N.D. | 15 | 0.3 | 0.3 | 1 |
| Example 11 | 1-1 | PSf/PVP(K30)/PVP(K90) 16/4/2 | DMAc/water 65/35 | 195/40 | 0.3/8.0 | a | Membranes were irradiated with γ-ray in mixed aqueous VP/VC(50/50) + Pro solution | $1.0 \times 10^{-8}$ | 28 | N.D. | 16 | 0.4 | 0.4 | 1 |

TABLE 1-continued

| | | Polymer composition of stock solution[2] [wt %] | Composition of injection solution [wt %] | inner diameter/ thickness [μm] | wave height/ wavelength [mm] | MD[3] No | Introduction of hydrophilic copolymerization polymer[4] | Relaxation time of adsorbed water [sec] | Amount of copolymerization polymer [wt %] Inner surface | Amount of copolymerization polymer [wt %] Outer surface | Inner surface flexible layer [nm] | Particulate protuberances [particles/ μm²] | Number of platelets adhered [particles/ (4.3 × 10³ μm²)] | Residual blood test [fiber membranes] |
|---|---|---|---|---|---|---|---|---|---|---|---|---|---|---|
| | HF[1] No | | | | | | | | | | | | | |
| Comparative Example 1 | 1-1 | PSf/PVP(K30)/ PVP(K90) 16/4/2 | DMAc/water 65/35 | 195/40 | 0.4/8.0 | a | None (Membranes were irradiated with γ-ray in mixed aqueous PVP + Et solution) | 2.6 × 10⁻⁸ | — | — | 5 | 0.3 | 70 | 25 |
| Comparative Example 2 | 4 | PSf/K90 17/5 | DMAc/water 57/43 | 190/45 | 0.4/8.0 | g | Membranes were irradiated with γ-ray in aqueous VP/VAc(70/30) solution | 2.2 × 10⁻⁸ | 13 | N.D. | 10 | 4.1 | 40 | 20 |
| Comparative Example 3 | 2-2 | PSf/PVP(K30)/ PVP(K90) 16/4/2 | DMAc/water VA64 63/37/10 | 200/40 | 0.2/8.0 | d-4 | VP/VAc(60/40) was added to injection solution | 1.6 × 10⁻⁸ | 15 | N.D. | 14 | 0.2 | 0.5 | more than 50 |
| Comparative Example 4 | 2-2 | PSf/PVP(K30)/ PVP(K90) 16/4/2 | DMAc/water VA64 63/37/10 | 200/40 | 0.2/8.0 | d-5 | VP/VAc(60/40) was added to injection solution | 1.6 × 10⁻⁸ | 15 | N.D. | 14 | 0.2 | 0.5 | 12 |
| Comparative Example 5 | 2-2 | PSf/PVP(K30)/ PVP(K90) 16/4/2 | DMAc/water VA64 63/37/10 | 200/40 | 0.2/8.0 | h | VP/VAc(60/40) was added to injection solution | 1.6 × 10⁻⁸ | 15 | N.D. | 14 | 0.2 | 0.5 | more than 50 |
| Comparative Example 6 | 1-2 | PSf/PVP(K30)/ PVP(K90) 16/4/2 | DMAc/water 65/35 | 200/40 | 0.2/8.0 | d-3 | None (Membranes were irradiated with γ-ray in mixed aqueous PVP + Et solution) | 2.6 × 10⁻⁸ | — | — | 5 | 0.3 | 67 | 20 |
| Comparative Example 7 | 1-1 | PSf/PVP(K30)/ PVP(K90) 16/4/2 | DMAc/water 65/35 | 195/40 | 0.3/8.0 | a | Membranes were irradiated with γ-ray in mixed aqueous VP/VC(50/50) + Pro solution | 1.0 × 10⁻⁸ | 33 | N.D. | 17 | 3.3 | 30 | 15 |

[1]HF: abbreviation for hollow fiber membrane,
[2]PSf: abbreviation for polysulfone, PVP: abbreviation for polyvinylpyrrolidone,
[3]MD: abbreviation for hollow fiber membrane module,
[4]VP: abbreviation for vinylpyrrolidone, VAc: abbreviation for vinyl acetate, VC: abbreviation for vinylcaprolactam, Pro: abbreviation for n-propanol, Et: abbreviation for ethanol, EG: abbreviation for ethylele glycol, PG: abbreviation for propylene glycol

TABLE 2

|  | Filling rate in outermost periphery [%] | Filling rate in center part [%] | Difference in filling rate between outermost and center part [%] | Ra of edge face part [μm] | Ra of header part [μm] | Sc-Alb(5) [%] | Sc-Alb(20) [%] | Sc-Alb(20)/ Sc-Alb(5) |
| --- | --- | --- | --- | --- | --- | --- | --- | --- |
| Example 1 | 47 | 62 | 15 | 0.2 | 0.5 | 1.01 | 0.77 | 0.76 |
| Example 2 | 47 | 62 | 15 | 0.2 | 0.5 | 0.88 | 0.73 | 0.83 |
| Example 3 | 47 | 62 | 15 | 0.2 | 0.5 | 0.75 | 0.66 | 0.88 |
| Example 4 | 30 | 58 | 28 | 0.2 | 0.5 | 0.98 | 0.77 | 0.79 |
| Example 5 | 48 | 63 | 15 | 0.2 | 0.5 | 1.65 | 1.22 | 0.74 |
| Comparative Example 1 | 47 | 62 | 15 | 0.2 | 0.5 | 1.5 | 0.83 | 0.55 |
| Comparative Example 2 | 22 | 52 | 30 | 0.9 | 0.5 | 4.24 | 2.04 | 0.48 |

|  | Sc-$\beta_2$MG(5) [%] | Sc-$\beta_2$MG(20) [%] | Sc-$\beta_2$MG(20)/ Sc-$\beta_2$MG(5) | Ko(W) [cm/min] | Ko(B) [cm/min] | Ko(B)/ Ko(W) |
| --- | --- | --- | --- | --- | --- | --- |
| Example 1 | 72.7 | 84.1 | 1.16 | 0.0711 | 0.0569 | 0.80 |
| Example 2 | 74.7 | 83.4 | 1.12 | 0.0666 | 0.0618 | 0.93 |
| Example 3 | 75.5 | 82.7 | 1.10 | 0.0612 | 0.0570 | 0.93 |
| Example 4 | 76.6 | 85.2 | 1.11 | 0.0666 | 0.0597 | 0.90 |
| Example 5 | 78.8 | 89.2 | 1.13 | 0.0687 | 0.0612 | 0.89 |
| Comparative Example 1 | 68.9 | 83.2 | 1.21 | 0.0711 | 0.0505 | 0.71 |
| Comparative Example 2 | 78.8 | 91.7 | 1.16 | 0.0711 | 0.0557 | 0.78 |

TABLE 3

|  | Header inner diameter D0 [mm] | Case body part inner diameter D1 [mm] | Fiber bundle outer diameter D2 [mm] | D0/D1 | Crimp amplitude W [mm] | Crimp pitch P [mm] | Filling rate in edge face [%] | Filling rate in body part [%] |
| --- | --- | --- | --- | --- | --- | --- | --- | --- |
| Example 6 | 37.3 | 35.1 | 36.7 | 1.063 | 0.1 | 8 | 54.1 | 61.1 |
| Example 7 | 37.3 | 35.1 | 36.3 | 1.063 | 0.85 | 17 | 54.1 | 61.1 |
| Example 8 | 35.1 | 35.1 | 34.3 | 1.000 | 0.1 | 8 | 61.1 | 61.1 |
| Example 9 | 37.3 | 35.1 | 36.7 | 1.063 | 0.1 | 8 | 54.1 | 61.1 |
| Example 10 | 37.3 | 35.1 | 36.7 | 1.063 | 0.1 | 8 | 54.1 | 61.1 |
| Comparative Example 3 | 37.3 | 35.1 | 35.4 | 1.063 | 0.1 | 8 | 54.1 | 61.1 |
| Comparative Example 4 | 37.3 | 35.1 | 36.7 | 1.063 | 0.1 | 8 | 54.1 | 61.1 |
| Comparative Example 5 | 44.3 | 35.1 | 41.2 | 1.262 | 0.1 | 8 | 38.4 | 61.1 |
| Comparative Example 6 | 37.3 | 35.1 | 36.7 | 1.063 | 0.1 | 8 | 54.1 | 61.1 |

|  | Filling rate in each zone[1) ] [%] | | | | | | | | | Residual blood test [tube] | Urea CL [mL/min] |
|  | A | B | C | D | E | F | G | H | average | | |
| --- | --- | --- | --- | --- | --- | --- | --- | --- | --- | --- | --- |
| Example 6 | 28.6 | 29.5 | 33.9 | 22.4 | 24.7 | 27.7 | 30.4 | 30.4 | 28.5 | 0 | 198 |
|  | 34.3 | 30.8 | 19.4 | 33.5 | 30.8 | 21.6 | 24.2 | 34.3 | 28.6 | | |
| Example 7 | 15.8 | 17.6 | 20.1 | 20.4 | 15.6 | 14.7 | 18.3 | 15.0 | 17.2 | 1 | 196 |
|  | 25.1 | 15.9 | 13.7 | 15.0 | 18.9 | 15.4 | 18.4 | 22.5 | 18.1 | | |
| Example 8 | 15.6 | 15.0 | 17.6 | 15.4 | 15.9 | 18.1 | 20.3 | 15.3 | 16.7 | 1 | 192 |
|  | 17.2 | 16.7 | 22.5 | 22.9 | 24.7 | 18.9 | 19.4 | 21.5 | 20.5 | | |
| Example 9 | 25.0 | 33.2 | 31.5 | 27.7 | 25.5 | 26.2 | 25.7 | 32.2 | 28.4 | 1 | 197 |
|  | 35.3 | 31.2 | 30.3 | 25.5 | 27.8 | 28.8 | 25.3 | 26.8 | 28.9 | | |
| Example 10 | 19.0 | 30.5 | 31.1 | 23.3 | 24.3 | 33.5 | 32.2 | 31.2 | 28.1 | 1 | 197 |
|  | 33.4 | 29.0 | 24.3 | 20.4 | 30.6 | 27.5 | 22.2 | 30.9 | 27.3 | | |
| Comparative Example 3 | 2.2 | 0.0 | 0.9 | 10.6 | 5.7 | 0.0 | 0.0 | 4.8 | 3.0 | more than 50 | 195 |
|  | 1.3 | 0.4 | 0.0 | 7.9 | 13.2 | 0.4 | 0.4 | 0.0 | 3.0 | | |
| Comparative Example 4 | 29.0 | 9.9 | 4.2 | 18.6 | 31.8 | 19.2 | 17.7 | 17.8 | 18.5 | 12 | 197 |
|  | 15.0 | 18.1 | 15.4 | 16.3 | 6.6 | 8.4 | 12.3 | 7.9 | 12.5 | | |
| Comparative Example 5 | 4.2 | 0.0 | 0.0 | 3.5 | 6.7 | 0.0 | 0.0 | 2.6 | 2.1 | more than 50 | 197 |
|  | 16.3 | 5.7 | 0.4 | 2.6 | 1.8 | 0 | 2.2 | 7.1 | 4.5 | | |

TABLE 3-continued

| Comparative | 33.3 | 29.3 | 23.3 | 32.4 | 27.0 | 25.3 | 30.1 | 29.9 | 28.8 | 20 | 196 |
| Example 6 | 26.6 | 28.7 | 20.8 | 30.5 | 29.9 | 34.9 | 22.1 | 34.1 | 28.5 | | |

[1] Uppper column: dividing wall edge face on blood inlet side (FIG. 1-31), lower column: dividing wall edge face on blood outlet side (FIG. 1-33)

DESCRIPTION OF REFERENCE SIGNS

1: Blood treatment apparatus
2: Case
3: Potting agent
4: Blood side inlet (Bi)
5: Blood side outlet (Do)
6: Dialyzate side inlet (Di)
7: Dialyzate side outlet (Do)
8: Hollow fiber membrane
10: Main body case
11: Baffle
12: Dialyzate inlet port
13: Dialyzate outlet port
21: Blood inlet header
22: Blood inlet port
23: Blood outlet header
24: Blood outlet port
25: Contact surface of header with partitioning wall
27, 28: Header internal space
30, 32: Partitioning wall
31, 33: Edge surface of partitioning wall
40: Hollow fiber membrane bundle
41: Hollow fiber membrane
58: Base line
59: Dialyzer
61: Bi pump
62: F pump
63: Waste container
64: Blood for circulation
65: Blood for clearance measurement
66: Bi circuit
67: Bo circuit
68: Di circuit
69: Do circuit
70: Warm water tank

The invention claimed is:

1. A hollow fiber membrane module comprising:
a hollow fiber membrane bundle which is composed of hollow fiber membranes, each hollow fiber membrane having, on a surface thereof which is to be in contact with blood, a hydrophilic copolymer having a relaxation time of adsorbed water of $2.5 \times 10^{-8}$ seconds or shorter and $5.0 \times 10^{-10}$ seconds or longer at $-40°$ C.;
a main body case in which the hollow fiber membrane bundle is stored;
partitioning walls which enable the hollow fiber membrane bundle to be held in a liquid-tight state at both ends of the main body case while keeping hollow fiber membranes in an opened state; and
headers which are respectively attached to both ends of the main body case and through which blood can be introduced and led out; and
zones A to H, which are produced by dividing a region lying between a position corresponding to the inner diameter (D0) of each of the headers and a position 1 mm apart from the aforementioned position toward the inner periphery into equal 8 parts equiangular with the center of axis of the main body case as its center in an edge face of each of the partitioning walls on a side facing each of the headers;
wherein each of zones A to H are configured to have a hollow fiber membrane packing density within the range from 13 to 40%, and the overall packing density of the edge face of each of the partitioning walls is within the range of 53 to 64%;
wherein the partitioning wall edge faces contain dispersed hollow fiber membranes,
wherein a flexible layer is present on the surface which is to be in contact with blood in each of the hollow fiber membranes when the hydrophilic copolymer is in a moistened state and the flexible layer has a thickness of 7 nm or more; and
wherein particulate protuberances each having a particle diameter of 50 nm or more are present on the surface which is to be in contact with blood in each of the hollow fiber membranes within a density range of from 0.1 particles/$\mu m^2$ to 3 particles/$\mu m^2$.

2. The hollow fiber membrane module according to claim 1, wherein the amount of the hydrophilic copolymer on the surface which is to be in contact with blood in each of the hollow fiber membranes is 5 to 30% by weight of the hollow fiber membrane.

3. The hollow fiber membrane module according to claim 1, each hollow fiber membrane having a crimp structure, and the wave height of the crimp structure is within the range from 0.1 mm to 1.5 mm.

4. The hollow fiber membrane module according to claim 1, each hollow fiber membrane having a crimp structure, and the wave length is within the range from 5 mm to 30 mm.

* * * * *